(12) United States Patent
Kim et al.

(10) Patent No.: US 11,746,372 B2
(45) Date of Patent: Sep. 5, 2023

(54) RAPID NUCLEIC ACIDS SEPARATION AND SAMPLE PREPARATION VIA HOLLOW-CENTERED SILICA MICROSPHERE

(71) Applicants: GoDX, inc., Madison, WI (US); The United States of America, as Represented by the Secretary, Department of Health and Human Services, Bethesda, MD (US)

(72) Inventors: Chang Hee Kim, Waunakee, WI (US); Lichen Xiang, Bethesda, MD (US); Wendy A. Henderson, Bethesda, MD (US); Xiao Jiang, Madison, WI (US)

(73) Assignees: GoDx, Inc., Madison, WI (US); The United States of America, as Represented by the Secretary, Dep. of Health and Human Services, Bethesda, MD (US)

( * ) Notice: Subject to any disclaimer, the term of this patent is extended or adjusted under 35 U.S.C. 154(b) by 0 days.

(21) Appl. No.: 16/768,802

(22) PCT Filed: Dec. 3, 2018

(86) PCT No.: PCT/US2018/063663
§ 371 (c)(1),
(2) Date: Jun. 1, 2020

(87) PCT Pub. No.: WO2019/109092
PCT Pub. Date: Jun. 6, 2019

(65) Prior Publication Data
US 2021/0180108 A1 Jun. 17, 2021

Related U.S. Application Data

(60) Provisional application No. 62/645,449, filed on Mar. 20, 2018, provisional application No. 62/593,598, filed on Dec. 1, 2017.

(51) Int. Cl.
*C12Q 1/6806* (2018.01)
*C12N 15/10* (2006.01)
*C12Q 1/6865* (2018.01)

(52) U.S. Cl.
CPC ....... *C12Q 1/6806* (2013.01); *C12N 15/1006* (2013.01); *C12Q 1/6865* (2013.01); *C12Q 2527/125* (2013.01); *C12Q 2531/113* (2013.01); *C12Q 2531/143* (2013.01); *C12Q 2563/155* (2013.01)

(58) Field of Classification Search
CPC ............... C12Q 1/6806; C12Q 1/6844; C12N 15/1003; C12N 15/1006
See application file for complete search history.

(56) References Cited

U.S. PATENT DOCUMENTS

| | | | |
|---|---|---|---|
| 5,770,416 A | 6/1998 | Lihme et al. | |
| 2002/0119482 A1* | 8/2002 | Nelson | B01L 3/502761 435/6.19 |
| 2004/0110167 A1 | 6/2004 | Gerdes et al. | |
| 2005/0016921 A1 | 1/2005 | Gjerde et al. | |
| 2006/0240448 A1* | 10/2006 | Bitner | C12N 1/02 435/6.12 |
| 2007/0015191 A1 | 1/2007 | Bitner et al. | |
| 2011/0117540 A1 | 5/2011 | Cary | |
| 2017/0131190 A1* | 5/2017 | Nakamura | C12N 15/1006 |
| 2018/0148774 A1 | 5/2018 | Kim et al. | |
| 2018/0304260 A1* | 10/2018 | Thomas | C12Q 1/6809 |

FOREIGN PATENT DOCUMENTS

| WO | 2007/095363 A2 | 8/2007 |
|---|---|---|
| WO | 2010/102294 A1 | 9/2010 |
| WO | 2015/095929 A1 | 7/2015 |
| WO | 2016/187160 A1 | 11/2016 |
| WO | 2017/075649 A1 | 5/2017 |
| WO | 2019/109092 A1 | 6/2019 |

OTHER PUBLICATIONS

Kulinski, M.D. et al., Sample preparation module for bacterial lysis and isolation of DNA from human urine, Biomed. Microdevices, vol. 11, pp. 671-678 (Year: 2009).*
Park, B.H. et al., An integrated rotary microfluidic system with DNA extraction, loopmediated isothermal amplification, and lateral flow strip based detection for point-of-care pathogen diagnostic, sBiosensors and Bioelectronics, vol. 91, pp. 334-340 (Year: 2017).*
"3M Glass Bubbles" Product Information, pp. 1-4 (Year: 2007).*
Zhao et al. Isothermal Amplification of Nucleic Acids. Chem. Rev. 2015, 115, 12491-12545.
Craw et al. Isothermal nucleic acid amplification technologies for point-of-care diagnostics: a critical review. Lab Chip, 2012,12,2469-2486.
International Search Report for PCT/US2018/063663 - Feb. 12, 2019.
Hsu et al. 14th International Conference on Miniaturized Systems for Chemistry and Life Sciences. 2010.
Liou et al. Buoyancy-Activated Cell Sorting Using Targeted Biotinylated Albumin Microbubbles. PloS one, 2015. 10(5): p. e0125036.

* cited by examiner

*Primary Examiner* — Teresa E Strzelecka
(74) *Attorney, Agent, or Firm* — Quarles & Brady LLP

(57) ABSTRACT

Disclosed herein are method for separating, amplifying, or detecting a nucleic acid from a sample may comprise contacting a sample lysate with a plurality of buoyant, inorganic, nucleic-acid-capture microspheres. The nucleic-acid-capture microspheres may comprise unicellular hollow microspheres having a diameter between 5 and 300 μm and/or a true particle density between 0.05 and 0.60 grams/cm$^3$. The microspheres may comprise hollow soda-lime-borosilicate microspheres. In some embodiments, the microspheres comprises hollow soda-lime-borosilicate microspheres surrounded by an amorphous silica shell. Also disclosed are kits for performing the methods.

9 Claims, 19 Drawing Sheets

Specification includes a Sequence Listing.

Fig. 3A
Fig. 3B
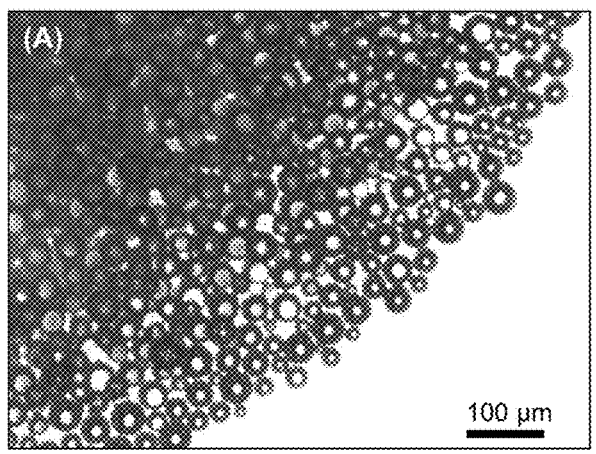
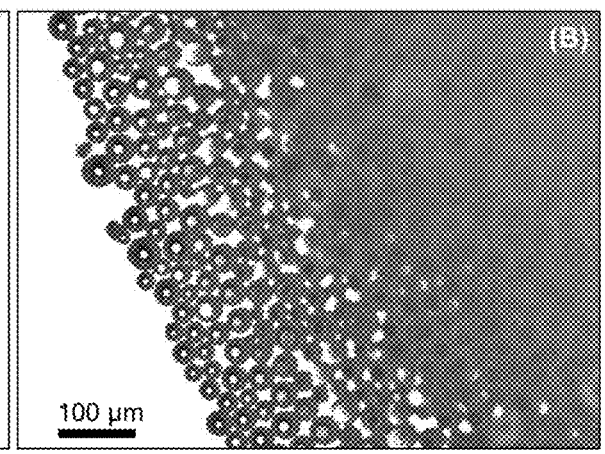
Fig. 4
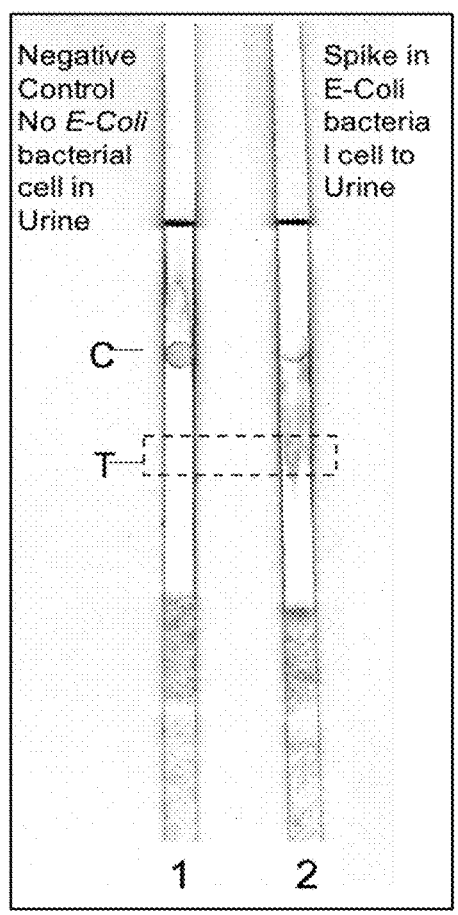

C. diff genomic DNA titration for LAMP reaction

Fig. 11A
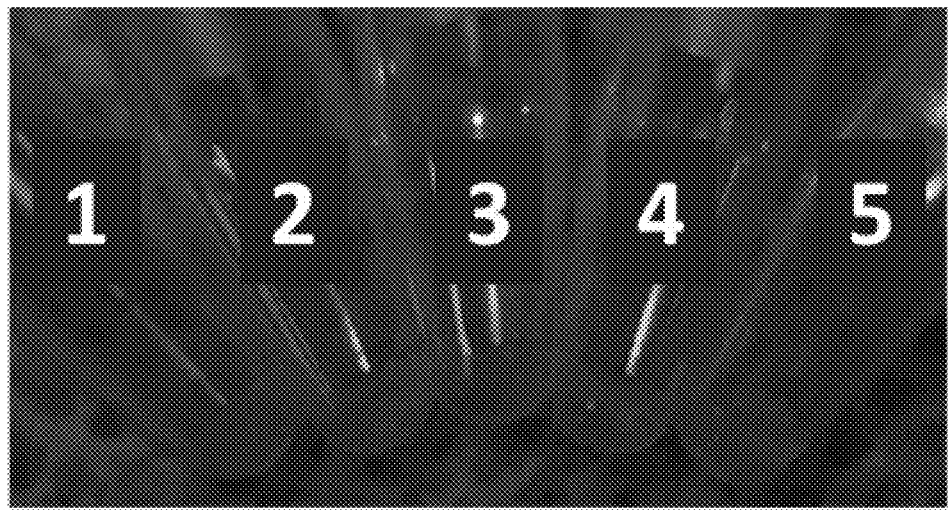
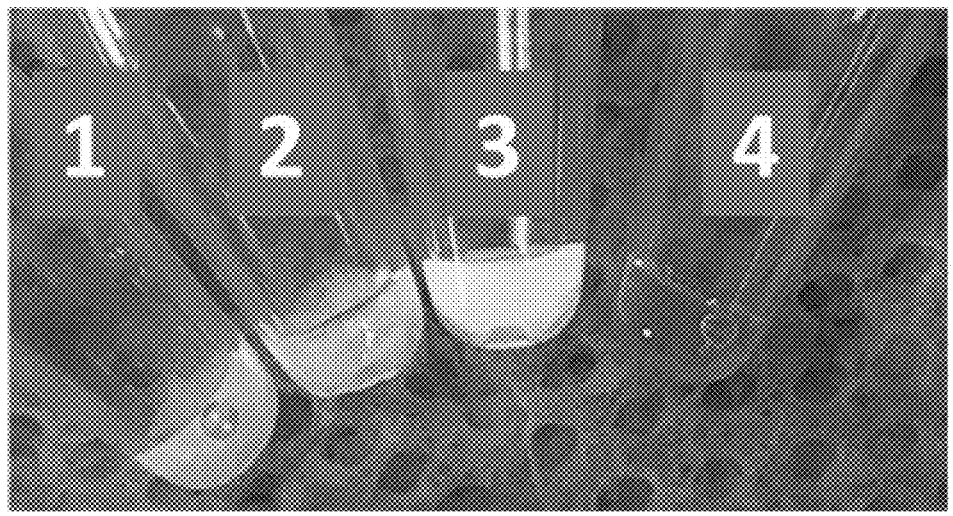
Fig. 11B

RAPID NUCLEIC ACIDS SEPARATION AND SAMPLE PREPARATION VIA HOLLOW-CENTERED SILICA MICROSPHERE

CROSS-REFERENCE TO RELATED APPLICATIONS

This patent application is a national stage filing under 35 U.S.C. § 317 of International Patent Application No. PCT/US2018/063663, filed Dec. 3, 2018, which claims the benefit of priority of U.S. Provisional Patent Application No. 62/593,598, filed Dec. 1, 2017, and U.S. Provisional Patent Application No. 62/645,449, filed Mar. 20, 2018, the contents of each are incorporated herein by reference in their entirety.

STATEMENT OF GOVERNMENT SUPPORT

This invention was created in the performance of a Cooperative Research and Development Agreement with the National Institutes of Health, an Agency of the Department of Health and Human Services and with government support under R44TR001912 awarded by National Institutes of Health and under 1ZIANR000018 awarded by the National Institutes of Health. The Government of the United States has certain rights in this invention.

REFERENCE TO A SEQUENCE LISTING

This application is being filed electronically via EFS-Web and includes an electronically submitted Sequence Listing in .txt format. The .txt file contains a sequence listing entitled "2018-12-03_6505-00007_ST25.txt" created on Dec. 3, 2018 and is 9,078 bytes in size. The Sequence Listing contained in this .txt file is part of the specification and is hereby incorporated by reference herein in its entirety.

FIELD OF INVENTION

The technology is generally directed to methods, compositions, systems, and kits for rapidly separating one or more nucleic acid target sequences from complex biological sample matrix. More specifically, the technology is directed to methods, compositions, systems, and kits for rapidly separating one or more nucleic acid target sequences from complex biological sample matrix using hollow-centered silica microspheres.

BACKGROUND

For point-of-need (PON) medical testing, sample preparation and detection must have rapid turnaround time, be easy to operate, be easy to port to the point of need, and be low-cost. Silica-based nucleic acid purification is one technique used to separate nucleic acids from complex mixtures. The method typically uses chaotropic salts to denature biomolecules and allows positively charged ions to form salt bridges between the negatively charged silica and nucleic acid backbone at high salt concentrations. The elution of the isolated nucleic acid molecules can be done by washing the silica-nucleic acid complex materials with a low ionic strength Buffer®. Silica-based separation methods, however, suffer from the following problems: they typically require electrically powered equipment, e.g., a centrifuge or vacuum, magnets, and expensive magnetic beads and are time-consuming and expensive to perform.

Buoyancy-activated separation is another separation method. The method was first reported for buoyancy-activated cell sorting (BACS) by Hsu et al. 14th International Conference on Miniaturized Systems for Chemistry and Life Sciences. 2010 and Liou et al. PloS one, 2015. 10(5): p. e0125036. BACS offers an alternative approach to separate circulating tumor cells and cancer stem cells from whole blood via hollow microbubbles (1-30 µm in diameter) functionalized with target-specific ligands to actively bind or capture the target cells and carry them to the top of the liquid. BACS, however, requires long separation times to separate specific cells, which would be against the principle of rapid diagnostic for PON applications. In addition, the buoyancy-activated separation concept is incapable of separating nucleic acids.

As a result, there exists a need for methods and devices capable of separating nucleic acids from complex biological matrices that avoid the use of expensive laboratory equipment, electric power, or professionally trained personnel.

BRIEF SUMMARY OF THE INVENTION

The present invention relates to methods, compositions, systems, and kits for rapidly separating one or more nucleic acid target sequences from a complex biological sample matrix, such as urine, stool, blood, or saliva. The methods utilize nucleic-acid-capture microspheres that are capable of binding to nucleic acids, allowing the nucleic acids to be rapidly and easily separated from complex matrices.

The method for separating a nucleic acid from a sample may comprise contacting a sample lysate with a plurality of buoyant, inorganic, nucleic-acid-capture microspheres to form a lysate dispersion; separating the lysate continuous phase from the particulate phase comprising a plurality of buoyant, inorganic, nucleic-acid-capture microspheres and the adsorbed nucleic acids obtained from the sample; and contacting the particulate phase with an eluent to form an eluate comprising the nucleic acid obtained from the sample. The nucleic-acid-capture microspheres may comprise unicellular hollow microspheres having a diameter between 5 and 300 µm and/or a true particle density between 0.05 and 0.60 grams/cm$^3$. The microspheres may comprise hollow soda-lime-borosilicate microspheres. In some embodiments, the microspheres comprises hollow soda-lime-borosilicate microspheres surrounded by an amorphous silica shell.

The lysate dispersion comprises a lysate continuous phase and a particulate phase and wherein the particulate phase comprises the plurality of buoyant, inorganic, nucleic-acid-capture microspheres and an adsorbed nucleic acid obtained from the sample. The lysate continuous phase and lysate particulate phases may be separating by various separation methodologies, including via extraction of the continuous phase, expulsion of the continuous phase, mechanical separation of the particulate phase, or absorption of the particulate phase. In some embodiments, the continuous phase is extracted from a sample collection vessel holding the lysate dispersion by drawing the continuous phase into a pipette or a syringe. In some embodiments, the lysate continuous phase is expelled from a pipette holding the dispersion or a syringe holding the lysate dispersion. In some embodiments, the particulate phase is mechanically separated by removing a semi-permeable container positioned within a sample collection vessel holding the dispersion from the sample collection vessel. In some embodiments, the particulate phase is adsorbed onto an absorptive pad contacting a meniscus formed of the lysate dispersion.

The method may further comprise one or more of the following: washing the particulate phase with a washing medium; providing the sample lysate; and/or separating the eluate from the plurality of buoyant, inorganic, nucleic-acid-capture microspheres.

In some embodiments, the washing step comprises contacting the particulate phase with the washing medium to form a washing dispersion and separating the washing continuous phase from the washing particulate phase. The washing continuous phase and washing particulate phases may be separating by various separation methodologies, including via extraction of the continuous phase, expulsion of the continuous phase, mechanical separation of the particulate phase, or absorption of the particulate phase.

In some embodiments, the providing the sample lysate step comprises contacting the sample with a lysis or denaturing agent to prepare the sample lysate. The sample may be any suitable sample, including stool, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mammary secretions, mucosal secretion, stool, stool water, pancreatic juice, lavage fluids from sinus cavities, bronchopulmonary aspirates, blastocyl cavity fluid, or umbilical cord blood.

Another aspect of the invention is a method for amplifying a nucleic acid obtained from a sample. The method may comprise separating a nucleic acid from a sample according to any of the methods described herein, contacting the nucleic acid separated from the sample with an amplification medium, and amplifying the nucleic acid separated from the sample. The nucleic acid may me amplified by a polymerase chain reaction (PCR) technique or an isothermal amplification technique. Isothermal amplifications techniques include Loop-mediated isothermal amplification (LAMP), Reverse-transcriptase loop-mediated isothermal amplification (RT-LAMP), Recombinase polymerase amplification (RPA), Strand displacement amplification (SDA), Helicase-dependent amplification (HDA), Nucleic acid sequence based amplification (NASBA), Nicking enzyme amplification reaction (NEAR), and transcription-mediated amplification (TMA).

In certain embodiments, the amplification medium comprises a primer complementary to a target sequence indicative of a pathogen or cell present in the sample. In particular embodiments, the pathogen is a prokaryotic pathogen, a eukaryotic pathogen, or a viral pathogen.

Another aspect of the invention is a method of detecting a nucleic acid in a sample indicative of a pathogen or a cell. The method may comprise separating a nucleic acid from a sample according to any of the methods described herein; contacting the nucleic acid separated from the sample with an amplification medium, wherein the amplification medium comprises a primer complementary to a target sequence indicative of the pathogen or the cell; amplifying the nucleic acid separated from the sample to form an amplified sample comprising a plurality of amplicons of the target sequence; and detecting the target sequence indicative of the pathogen or the cell. In some embodiments, the detecting step comprises: loading a lateral flow device; and detecting a trimolecular hybridization of (1) the target sequence, (2) a detectably labelled probe specific for the target sequence, and (3) a capture probe for the target sequence. In some embodiments, the lateral flow device may be loaded with the amplified sample, the eluate, or a particulate phase. In some embodiments, the lateral flow device is a multiplexed lateral flow device comprising a multiplicity of lateral flow devices. In certain embodiments, the target sequence comprises a multiplicity of target sequences indicative of one or more pathogens and the multiplicity of target sequences is less than or equal to the multiplicity of lateral flow devices.

Another aspect of the invention comprises a kit. The kit may be used to perform any of the methods described herein. The kit may comprise a plurality of buoyant, inorganic, nucleic-acid-capture microspheres and one or more of: a eluent; a lysis or denaturing agent; a washing medium; a amplification medium; a swab; a sample collection vessel; a microsphere separation device; a nucleic acid collection vessel; an amplification device; a testing device; and a control nucleic acid.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 3A and 3B show 10× magnitude of the bright-field and epi-fluorescence overlay images for (FIG. 3A) control microspheres without Alexa 488 fluorescent dye pre-labeled DNA oligonucleotides and (FIG. 3B) fluorescent dye pre-labeled DNA oligonucleotides bound to the microsphere after 10 min incubation.

FIG. 4 shows paper strips in which *E. coli* cells ($1 \times 10^6$ cells) are lysed and purified using hollow microspheres prior to application on paper.

FIGS. 11A and 11B show norovirus RNA detection using RT-LAMP from diluted (FIG. 11A) and microsphere-extracted (FIG. 11B) stool matrix sample. (FIG. 11A): Detection result of diluted stool matrix sample. Tubes 1-4 (dark) are 1/10, 1/50, 1/100 and 1/500 dilutions of stool matrix respectively. Tube 5 (dark) is a negative control. (FIG. 11B): Detection result of RNA extracted from stool matrix using microspheres. Tube 1-3 (green) are the RNA elution, 1/2 and 1/10 dilution of the RNA elution respectively. Tube 4 (dark) is a negative control.

DETAILED DESCRIPTION OF THE INVENTION

Figure 1:
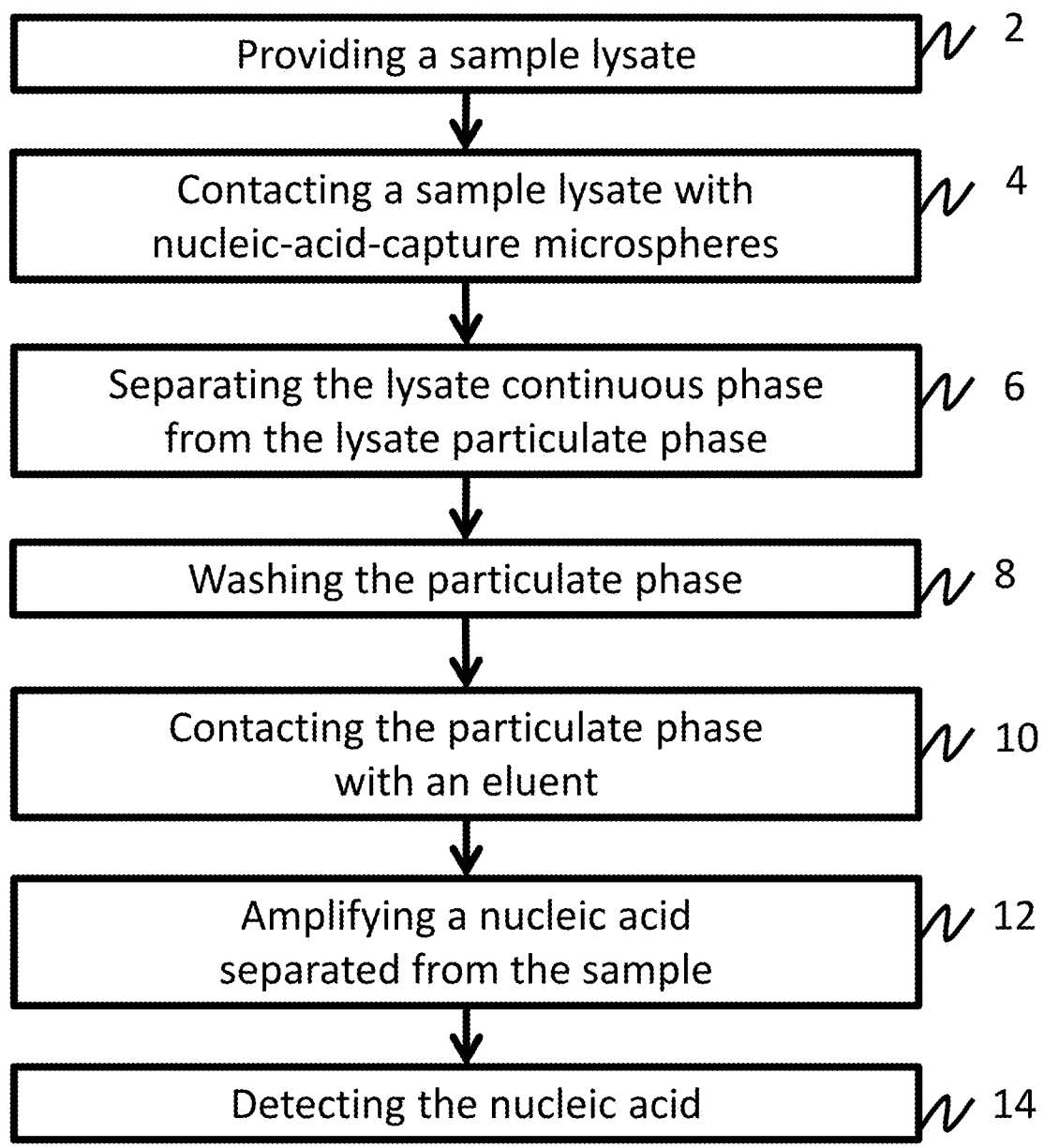
FIG. 1 illustrates the use of microspheres for the detection of nucleic acids obtained from a sample.

The present invention relates to methods, compositions, systems, and kits for rapidly separating one or more nucleic acid target sequences from a complex biological sample matrix, such as urine, stool, blood, saliva, tissues, or environmental samples. The methods utilize nucleic acid capture microspheres that are capable of binding to nucleic acids, allowing the nucleic acids to be rapidly and easily separated from complex matrices. The separation method is rapid, easy to perform, portable, low-cost, and does not require expensive laboratory equipment, power, or professionally trained personnel. Moreover, the technology integrates with PON diagnostic devices, such as lateral flow devices, enabling the sample-to-answer diagnostics and increasing the purity of the analyte to improve diagnostic signals. As a result, the technology is suitable for PON medical and environmental testing.

Definitions

Amplification Medium

As used herein, an "amplification medium" is a composition for use in the production of amplicons of a target nucleic acid sequence by nucleic acid amplification. As used herein, an "amplicon" means a piece of DNA or RNA that is the source and/or product of nucleic acid amplification. The amplicon may be produced by any amplification technique, including a polymerase chain reaction (PCR) technique or an isothermal amplification technique. Exemplary isothermal amplification techniques include, without limitation, Loop-mediated isothermal amplification (LAMP), Reverse-transcriptase loop-mediated isothermal amplification (RT-LAMP), Recombinase polymerase amplification (RPA), Strand displacement amplification (SDA), Helicase-dependent amplification (HDA), Nucleic acid sequence based amplification (NASBA), Nicking enzyme amplification reaction (NEAR), and transcription-mediated amplification (TMA). Details of such isothermal amplification techniques can be found in Zhao et al. Chem. Rev. 2015, 115, 12491-12545 and Craw and Balachandran Lab Chip, 2012,12, 2469-2486.

The amplification medium may comprise a polymerase, a primer, nucleoside triphosphates, a cofactor, a buffering agent, a solvent, a amplification enhancer, or any combination thereof. As used herein, a "polymerase" is an enzyme capable of catalyzing the formation of nucleic acids. The polymerase may be a DNA polymerase or an RNA polymerase. Suitably, the polymerase may be selected from a Taq polymerase or a Bst polymerase.

As used herein, a "primer" means a nucleic acid designed to bind via sequence complementarity to sequences that flank the target sequence in the template nucleic acid. During amplification, polymerases extend the primers. As such, the primer's binding site should be unique to the vicinity of the target sequence with minimal homology to other sequences to ensure specific amplification of the intended target sequence.

Nucleoside triphosphates are present for the formation of nucleic acids. The nucleoside triphosphates may include deoxynucleoside triphosphates (dNTPs), e.g., dATP, dCTP, dGTP, and dTTP.

As used herein, a "cofactor" means a substance other than the substrate that is essential for the activity of an enzyme. Suitably, the cofactor may be $Mg^{2+}$ which functions as a cofactor for the activity of a variety of polymerases, enabling the formation of nucleic acids during polymerization. The cofactor may be introduced to the amplification medium as a salt, e.g., $MgSO_4$ or $MgCl_2$.

As used herein, a "buffering agent" comprises a weak acid or base used to maintain the acidity (pH) of a solution near a chosen value after the addition of another acid or base. Suitably, the buffering agent may be selected from Tris-HCl, $(NH_4)_2SO_4$, or KCl.

The solvent may be selected from any suitable solvent or combination of solvents that allow for application. Suitably, the solvent is water. An amplification medium without a solvent may be referred to as a "dry amplification reagent."

As used herein, an "amplification enhancer" is a substance that may enhance amplification specificity, efficiency, consistency, and/or yield. Suitably, the amplification enhancer comprises dimethyl sulfoxide, glycerol, formamide, polyethylene glycol, N,N,N-trimethylglycine (betaine), bovine serum albumin, tetramethylammonium chloride, a detergent, or combinations thereof. Suitably, the detergent is a nonionic detergent such as Tween 20 or Triton X-100.

Dispersion

As used herein, a "dispersion" is a two-phase system comprising a particulate phase, e.g., the microspheres, and any compositions adsorbed or bound thereto, dispersed in a continuous phase, e.g., a liquid. The dispersions prepared from microspheres are unstable and rapidly aggregate. Because the microspheres are buoyant, instead of settling due to the influence of gravity, the microspheres aggregate at the surface of the continuous phase. This allows for the particulate phase and the continuous phase to be easily separated from each other.

Eluent

As used herein, an "eluent" is a material used to extract nucleic acids adsorbed or bound onto the surface of microspheres from the surface. The "eluate" is the composition comprising the extracted nucleic acids. The eluent may be any suitable material for extracting the nucleic acids from the microspheres. Exemplary eluents include, without limitation, water, 50 mM NaCl, TE buffer (10 mM Tris brought to pH 8.0 with HCl, 1 mM EDTA), or any combination thereof.

Lateral Flow Device

As used herein, a "lateral flow device" is a porous device capable of detecting the presence of a target sequence traversing a series of beds. Lateral flow devices comprise (a) a sample loading area at one end of the lateral flow device; (b) an area comprising a detectably labelled probe specific for a target nucleic acid sequence, wherein said detectably labelled probe is not bound to the lateral flow device and is capable of wicking across the lateral flow device; (c) an area comprising a capture probe for the target nucleic acid sequence, wherein said capture probe for the target nucleic acid sequence is immobilized on the lateral flow device; and (d) absorbent material, wherein the absorbent material wicks an aqueous sample across the lateral flow device when the aqueous sample is added to the sample loading area. In some embodiments, the capture probe is capable of moving toward the area comprising the detectably labelled probe either by movement of the capture probe itself (i.e., the capture probe is not immobilized), or by movement of the area comprising the capture probe. Details of such a method can be found in United States Patent Publication No. 2018/0148774, incorporated by reference herein.

In some embodiments, the lateral flow device further comprises an amplification area. The amplification area comprises a dry amplification medium immobilized within the amplification area. The amplification area may be loaded with an eluate comprising a target nucleic acid sequence. Under appropriate temperature conditions, the target nucleic acid sequence may be amplified and the amplicons detected.

The sample loading area may comprise a material that traps debris. The debris may comprise a component of a lysed or unlysed biological sample, an eluate, or a microsphere. In some embodiments, the material comprises glass fiber. In some embodiments, the material comprises polyester and/or cellulose. In some embodiments, the material that traps debris is any commercially available microporous material. As used herein, "traps" or "trapping" refers to immobilizing, delaying movement, capturing (temporarily or permanently), impeding movement, or hindering movement. As used herein, "debris" means any particulate matter other than the components of the disclosed assays or devices. In some embodiments, "debris" includes tissue, food particles, clumped cells, cell walls, microspheres, and the like.

In some embodiments, the sample loading area is a microsphere-loading area. As used herein, a "microsphere-loading area" comprises material that traps microspheres transferred onto or into the microsphere-loading area and also allows for an eluate to traverse the microsphere-loading area when an eluent contacts trapped microspheres having nucleic acids adsorbed thereto. When the lateral flow device comprises a microsphere-loading area, the lateral flow device may also comprise an amplification area for amplifying nucleic acids within the eluate extracted from the microspheres trapped on or in the microsphere-loading area.

The lateral flow device may comprise a solid support such as a paper. Suitably, the solid support comprises cellulose, such as filter paper, chromatographic paper, nitrocellulose, and cellulose acetate. In some embodiments, the solid support comprises materials such as glass fibers, nylon, dacron, PVC, polyacrylamide, cross-linked dextran, agarose, polyacrylate, ceramic materials, and the like.

The lateral flow device may comprise an absorbent sample pad infused with the gold conjugated detection probe, a lateral flow channel which contains the spotted streptavidin fixed biotinylated capture probe on the test area and spotted streptavidin fixed biotinylated control probe on the control area.

The conjugation area comprises a detectably labelled probe specific for a target nucleic acid sequence, wherein said detectably labelled probe is not bound to the lateral flow device and is capable of wicking across the lateral flow device.

The detectably labelled probe specific for a target nucleic acid sequence may be labeled with a moiety selected from a gold nanoparticle, a protein binding ligand, a hapten, an antigen, a fluorescent compound, a dye, a radioactive isotope and an enzyme. In some embodiments, the detectably labelled probe is labelled with a gold nanoparticle. In some embodiments, the detectably labelled probe is labelled with latex beads, latex microspheres and/or magnetic beads.

Choosing and designing the sequence of the probe specific for a target nucleic acid sequence is based on the nature of the source of the target nucleic acid sequence. Generally, the probe specific for the target nucleic acid that will be detectably labelled is capable of specifically hybridizing to part of the target nucleic sequence, separate from the sequence to which the capture probe will specifically hybridize.

Exemplary nucleic acid detection probes, control probes, capture probes have been designed for each target pathogens including *E. coli, C. diff, Campylobacter, Cryptosporidium,*

*Giardia*, Norovirus, ETEC, and EPEC. The details of the probe sequences are listed in Table 1.

TABLE 1

DNA probes of eight pathogens for lateral flow diagnostic device

| Oligo Name | 5' Mod | Sequence | 3' Mod |
|---|---|---|---|
| *E. coli* | | | |
| E-DC | | GAG CGT TCT GTA AGC CTG CGA AAA AAA AA (SEQ ID NO: 1) | [BtnTg] |
| E-C | [Btn] | AA AAA AAA TAC CTC CAG CAT GCC TCA CAG (SEQ ID NO: 2) | |
| E-D | | TCG CAG GCT TAC AGA ACG CTC AAA AAA AA (SEQ ID NO: 3) | [ThiC3] |
| *C. diff* | | | |
| CD-DC | | CCA CAT GTC CTT ACG GTC ATG AAA AAA AA (SEQ ID NO: 4) | [BtnTg] |
| CD-C | [Btn] | AA AAA AAA GTA GGG GAG CTT CCC ATA CGG (SEQ ID NO: 5) | |
| CD-D | | CAT GAC CGT AAG GAC ATG TGG AAA AAA AA (SEQ ID NO: 6) | [ThiC3] |
| *Cryptosporidium* | | | |
| CRF-DC | | AGC CTG AGA AAC GGC TAC CAC ATC AAA AAA AA (SEQ ID NO: 7) | [BtnTg] |
| CRF-C | [Btn] | AA AAA AAA GTA ATT GCG CCT GCT GCC (SEQ ID NO: 8) | |
| CRF-D | | GAT GTG GTA GCC GTT TCT CAG GCT AAA AAA AA (SEQ ID NO: 9) | [ThiC3] |
| *Giardia* | | | |
| GRD-DC | | GTC AAG CTC AGC AAC ATG AAC AAA AAA AA (SEQ ID NO: 10) | [BtnTg] |
| GRD-C | [Btn] | AA AAA AAA TCT TGT CGT GGA ACC TGC TGA (SEQ ID NO: 11) | |
| GRD-D | | GTT CAT GTT GCT GAG CTT GAC AAA AAA AA (SEQ ID NO: 12) | [ThiC3] |
| *Campylobacter* | | | |
| Camp-DC | | CAC AAG TTG AGT AGG GAA AGT AAA AAA AA (SEQ ID NO: 13) | [BtnTg] |
| Camp-C | [Btn] | AA AAA AAA ACT ATA TAG TCT CAT CCT ACA (SEQ ID NO: 14) | |
| Camp-D | | ACT TTC CCT ACT CAA CTT GTG AAA AAA AA (SEQ ID NO: 15) | [ThiC3] |
| *Norovirus* | | | |
| Noro-DC | | ATG ATG CAG ACT ACT CTC GTT AAA AAA AA (SEQ ID NO: 16) | [BtnTg] |
| Noro-C | [Btn] | AA AAA AAA AGT ACT GCC CTC TGT TGT GTT (SEQ ID NO: 17) | |
| Noro-D | | AAC GAG AGT AGT CTG CAT CAT AAA AAA AA (SEQ ID NO: 18) | [ThiC3] |
| *ETEC* | | | |
| ETEC TOX-DC | | ATC TTT CCC CTC TTT TAG TCA AAA AAA AA (SEQ ID NO: 19) | [BtnTg] |
| ETEC TOX-C | [Btn] | AA AAA AAA TTT TGA AGA GTC AAG TGA TTC (SEQ ID NO: 20) | |

TABLE 1-continued

DNA probes of eight pathogens for lateral flow diagnostic device

| Oligo Name | 5' Mod | Sequence | 3' Mod |
|---|---|---|---|
| ETEC TOX-D | | TGA CTA AAA GAG GGG AAA GAT AAA AAA AA (SEQ ID NO: 21) | [ThiC3] |
| EPEC | | | |
| EPEC-DC | | CAG CCC GGA GGG CTG CAT TAC AAA AAA AA (SEQ ID NO: 22) | [BtnTg] |
| EPEC-C | [Btn] | AA AAA AAA GCT CGG CTT TCA GCC CTC TTG (SEQ ID NO: 23) | |
| EPEC-D | | GTA ATG CAG CCC TCC GGG CTG AAA AAA AA (SEQ ID NO: 24) | [ThiC3] |

The test area comprises a capture probe for the target nucleic acid sequence, wherein said capture probe for the target nucleic acid sequence is immobilized on the lateral flow device, is also called the test probe area. The test area can be in any form with well-defined boundaries, such as a dot, or a strip. The capture probe may be immobilized on the lateral flow device by covalent coupling or affinity binding. Suitably, the capture probe is attached to the lateral flow device by biotin: streptavidin affinity binding. Generally, the capture probe is capable of specifically hybridizing to part of the target nucleic acid sequence, separate from the sequence to which the detectably labelled probe will bind.

The lateral flow device may comprise an area comprising a control probe, wherein said control probe is immobilized on the lateral flow device. This area is also called the control area, or the control probe area. The control probe may comprise a sequence complementary to the detectably labelled probe. The control probe may be immobilized on the lateral flow device by covalent coupling or affinity binding. Suitably, the control probe is attached to the lateral flow device by biotin: streptavidin affinity binding.

The absorbent material which wicks an aqueous sample across the lateral flow device may comprise cellulose. Suitably the cellulose is selected from filter paper, chromatographic paper, nitrocellulose, and/or cellulose acetate. As used herein, a material that "wicks" an aqueous sample refers to any structure, material, and/or device, etc., that permits movement and/or transportation of an aqueous sample and at least some of its contents, or that permits the aqueous sample to contact the test and/or control areas of the disclosed devices.

In some embodiments, the absorbent material is in the form of an absorbent pad at the end of lateral flow device opposite of the sample loading area. In other embodiments, the absorbent material runs the length of the lateral flow device.

The lateral flow device may be capable of multiplex nucleic acid detection (i.e., the point of need testing device comprises at least two, at least three, at least four, at least five, at least six, at least seven, at least eight, at least nine, at least ten, at least eleven, at least twelve, at least thirteen, at least fourteen, at least fifteen, at least twenty, or at least twenty five lateral flow devices). In some embodiments, each lateral flow device comprises a probe specific for a different target nucleic acid (e.g., a different microorganism or virus).

In some embodiments, the plurality of lateral flow devices are arranged in a radial manner (i.e., similar to a star). In some embodiments, the lateral flow devices are arranged in a radial manner around a central sample loading area. For example, in one embodiment the point of need device is a star-shaped multiplex paper strip. In some embodiments, thin sheets of porous nitrocellulose membranes are cut into star shapes using a computer-controlled X-Y knife plotter cutter. This device incorporates a knife in place of the traditional ink pen. The knife rotates freely on a turret, enabling precise cutting of various features. The control lines (containing the control probe) and test lines (containing the detection probe) will be spotted on each of the arms. The lateral flow paper strips are spotted using a BioDot AD1520 tabletop aspirating/dispensing workstation outfitted with two BioJet™ Elite dispensers capable of generating overlapping spots within nitrocellulose (minimal volumes of 20-50 nL) or continuous reagent lines (1 μL/cm). Dispensing protocols are custom written for the snowflake nitrocellulose design and optimized for buffer conditions, dispense volume, and spatial separation.

In some embodiments, the plurality of lateral flow devices are arranged in a lateral manner.

In some embodiments, the plurality of lateral flow devices are micropatterned onto the point of care device by a method of patterning a porous, hydrophilic substrate into hydrophobic and hydrophilic regions. In some embodiments, such a method comprises disposing a wax material onto the hydrophilic substrate in a predetermined pattern; and heating the substrate to a temperature sufficient to melt the wax material, the melted wax material substantially permeating the thickness of the substrate and defining a pattern of one or more hydrophobic regions. Details of such a method can be found in International Patent Publication No. W2010/102294, incorporated by reference herein.

Microsphere-Retaining Mesh

As used herein, a "microsphere-retaining mesh" is a mesh having a plurality of openings large enough to allow for the movement of nucleic acids through the mesh but small enough to prevent the majority of microspheres from moving across the mesh. Suitably the mesh may have openings less than 250 microns, 180 microns, 150 microns, 125 microns, 106 microns, 75 microns, 63 microns, 53 microns, 45 microns, 38 microns, 25 microns, 20 microns, 15 microns, 10 microns, or 5 microns. Alternately, the meshes may be described by the Tyler mesh sizes of 60, 80, 100, 115, 150, 170, 200, 250, 270, 325, 400, 500, 625, 800, 1250, or 2500.

Microsphere-Separating Device

As used herein, a "microsphere-separating device" means a device capable of separating a continuous phase from a particulate phase comprising microspheres, with or without nucleic acids adsorbed thereon.

Suitably, the microsphere-separating device may comprises a device capable of generating a vacuum to extract a continuous phase from a vessel. Exemplary microsphere-separating devices of this type include, without limitation, droppers, pipettes, or syringes. Such devices may suitably comprise a microsphere-retaining mesh position to prevent microspheres from entering the device.

Suitably, the microsphere-separating device may comprises a device capable of generating a pressure to expel a continuous phase from a vessel. Exemplary microsphere-separating devices of this type include, without limitation, droppers, pipettes, or syringes. Such devices may suitably comprise a microsphere-retaining mesh position to prevent microspheres from being expelled from the device with the continuous phase.

Suitably, the microsphere-separating device may comprise a device capable of mechanically separating the particulate phase from a continuous phase. Exemplary microsphere-separating devices of this type include, without limitation, semi-permeable container. As used herein, a "semi-permeable container" means is a container having a plurality of openings large enough to allow for the movement of nucleic acids and liquids into and out of the container but small enough to prevent a majority of microspheres from escaping the container. Such devices may suitably comprise a microsphere-retaining mesh positioned to prevent microspheres from escaping the container.

Suitably, the microsphere-separating device may comprise a device capable of having microspheres adsorbed thereon. Exemplary microsphere-separating devices of this type include, without limitation, microsphere-loading areas.

Nucleic-Acid-Capture Microspheres

The present technology utilizes nucleic-acid-capture microspheres. As used herein, "nucleic-acid-capture microspheres" comprise microspheres capable of binding nucleic acids in a complex matrix and releasing them when contacted with an eluent. The nucleic-acid-capture microspheres may be referred to as "glass bubbles", "hollow microspheres", or, simply, "microspheres". Nucleic-acid-capture microspheres are typically unicellular, but may contain some microspheres having a plurality of internal voids separated by extremely thin veils. The microspheres may vary in diameter from a few microns to hundreds of microns, e.g., approximately 5-300 microns, 5-200 microns, or 10-100 microns. The exterior wall thickness of the microspheres varies, usually from approximately 5% to about 20% of the diameter of a complete microsphere or a faction of a micron (e.g., 0.5 microns) to several microns (e.g., 5 microns). The microspheres are typically buoyant. As used herein, "buoyant" means that the majority of the microspheres have an average true density lower than water, typically from about 0.05-0.60 grams/cm$^3$, 0.10-0.40 grams/cm$^3$, or about 0.15-0.30 grams/cm$^3$. An "average true density" is determined by placing microspheres in a chamber which is filled with air under compression. The air volume in that chamber is compared with the air volume in an identical sized chamber in which air is under equal compression. The difference in air volume is recorded; and the true volume occupied by the bubbles is calculated. The average true particle density is obtained by dividing the true volume occupied by the bubble sample into the weight of the sample.

The compositions of the microspheres may vary but are typically inorganic. As used herein, "inorganic" means that the microspheres are substantially free of carbon. Suitably the ingredients used to prepare the microspheres include at least some SiO$_2$, a fixing ingredient such as an alkali metal oxide, and one or more bivalent, trivalent, quadrivalent, or pentavalent oxides so that the inorganic components provide a composition which melts to form a glass at a temperature between approximately 1200° C.-1500° C. Suitably, soda-lime-silica or soda-lime-borosilicate glasses may be used to prepare the microspheres. In some embodiments, the microspheres for use in practicing the invention have a compositional analysis within the approximate ranges set forth in Table 2.

TABLE 2

Exemplary compositional analysis of nucleic-acid-capture microspheres

| Ingredient | Weight percent |
|---|---|
| SiO$_2$ | 60-80 |
| Na$_2$O | 5-16 |
| CaO | 5-25 |
| K$_2$O + Li$_2$O | 0-10 |
| Na$_2$O + K$_2$O + Li$_2$O | 5-16 |
| RO (other than CaO) | 0-15 |
| RO$_2$ | 0-10 |
| R$_2$O$_3$ | 0-20 |
| R$_2$O$_5$ | 0-25 |
| F | 0-5 |

Suitably, RO is selected from alkaline earth oxides (e.g., BaO, MgO, and SrO) as well as bivalent oxides such as ZnO and PbO;
RO$_2$ is selected TiO$_2$, MnO$_2$, and ZrO$_2$;
R$_2$O$_3$ is selected from B$_2$O$_3$, Al$_2$O$_3$, Fe$_2$O$_3$, and Sb$_2$O$_3$;
R$_2$O$_5$ is selected from P$_2$O$_5$ and V$_2$O$_5$; or any combination thereof.

In some embodiments, the microspheres comprise a silica shell completely or partially surrounding the microsphere compositions described above. Suitably, the silica shell may comprise between about 1-20 weight percent, 1-10 weight percent, or about 1-5 weight percent of the microsphere. The silica shell may be amorphous but need not be.

Exemplary microspheres include glass bubbles from 3M™ such as the glass bubbles described in Table 3.

TABLE 3

Exemplary nucleic-acid-capture microspheres

| | Target crush strength (90% survival, psi) | True density (g/cm$^3$) | Typical particle size (microns, by volume) Distribution: | | |
|---|---|---|---|---|---|
| | | | 10th % | 50th % | 90th % |
| K1 | 250 | 0.125 | 30 | 65 | 115 |
| K15 | 300 | 0.15 | 30 | 60 | 105 |
| S15 | 300 | 0.15 | 25 | 55 | 90 |
| S22 | 400 | 0.22 | 20 | 35 | 65 |
| K20 | 500 | 0.2 | 25 | 55 | 95 |
| K25 | 750 | 0.25 | 25 | 55 | 90 |
| S32 | 2000 | 0.32 | 20 | 40 | 70 |
| S35 | 3000 | 0.35 | 10 | 40 | 75 |
| K37 | 3000 | 0.37 | 20 | 45 | 80 |
| XLD3000 | 3000 | 0.23 | 15 | 30 | 40 |
| S38 | 4000 | 0.38 | 15 | 40 | 75 |
| S38HS | 5500 | 0.38 | 15 | 40 | 75 |
| S38XHS | 5500 | 0.38 | 15 | 40 | 70 |
| K46 | 6000 | 0.46 | 15 | 40 | 70 |
| K42HS | 7500 | 0.42 | 11 | 22 | 37 |
| S60 | 10000 | 0.6 | 15 | 30 | 55 |
| S60HS | 18000 | 0.6 | 11 | 30 | 50 |
| IM16K | 16000 | 0.46 | 12 | 20 | 30 |
| IM30K | 28000 | 0.6 | 9 | 16 | 25 |

As demonstrated in the examples that follow, K$_2$O and XLD3000 where successfully used to separate nucleic acids from complex samples. The chemical composition of both $K_2O$ and XLD3000 glass bubbles is 97% soda lime borosilicate glass and 3% synthetic amorphous crystalline free silica at the bubble surface.

Advantageously, the microspheres nonspecifically bind nucleic acids. This allows for the microspheres to be used to separate a variety of nucleic acids without having to be tailored for a specific target. As a result, the microspheres of the present invention do not require target-specific binding moieties, such as nucleic acids or proteins, to be bound to the surface of the microspheres.

As demonstrated in the examples, compositions having an organic surface fail to successfully separate nucleic acids. Without wishing to be bound by theory, it is believed that positively charged ions are capable of forming salt bridges between the inorganic surface and negatively-charged nucleic acid backbone. When microspheres possess, for example, an epoxy silane surface treatment, the microspheres fail to separate nucleic acids. Thus, carbon at the surface of the microsphere interferes with its nucleic acid binding capability.

Nucleic Acids

As used herein, "nucleic acids" mean unmodified or modified DNA or unmodified or modified RNA. The DNA may be genomic DNA (e.g., DNA encoding a protein, open reading frames, or regulatory sequences), mitochondrial DNA, extracellular DNA, plasmid DNA, or cell-free fetal DNA. The RNA may be involved in protein synthesis, involved in post-transcriptional modification, DNA replication, or regulation. RNAs involved in protein synthesis may include, without limitation, mRNAs, rRNAs, tRNAs, or SRP RNAs. RNAs involved in post-transcriptional modification may include, without limitation, snRNAs, snoRNAs, or Y RNAs. Regulatory RNAs may include, without limitation, antisense RNAs, CRISPR RNAs, guide RNAs, long noncoding RNAs, microRNAs, siRNAs, piRNAs, tasiRNAs, 5'UTR sequences, 3'UTR sequences, RNA splicing regulatory sequences, IRES sequences, or polyA signal sequences.

Pathogen

As used herein, a "pathogen" is any microorganism capable of causing disease in a subject. A "subject" may be interchangeable with "patient" or "individual" and means an animal, which may be a human or non-human animal, in need of treatment. A "subject in need of treatment" may include a subject having a disease caused by a pathogen.

Suitably the pathogen may be a prokaryotic pathogen, a eukaryotic pathogen, or a viral pathogen. In some embodiments, pathogen is selected from *Escherichia, Campylobacter, Clostridium difficile*, Enterotoxigenic *E. coli* (ETEC), Enteroaggregative *E. coli* (EAggEC), Shiga-like Toxin producing *E. coli, Salmonella, Shigella, Vibrio cholera, Yersinia enterocolitica*, Adenovirus, Norovirus, Rotavirus A, *Cryptosporidium parvum, Entamoeba histolytica, Giardia lamblia*, Clostridia, Methicillin-resistant *Staphylococcus aureus* MRSA, *Klebsiella pneumonia*, flu, Zika, dengue, chikungunya, West Nile virus, Japanese encephalitis, malaria, HIV, H1N1, and *Clostridium difficile* resistant organisms.

Sample

As used herein, a "sample" is a substance that comprises or may comprise nucleic acids. The sample may be a biological sample obtained from a subject. Suitably, the biological sample may comprise stool, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mammary secretions, mucosal secretion, stool, stool water, pancreatic juice, lavage fluids from sinus cavities, bronchopulmonary aspirates, blastocyl cavity fluid, and umbilical cord blood. In some embodiments, the sample is a gastrointestinal fluid. In some embodiments, the biological sample is stool. In some embodiments, the biological sample is selected from a skin swab sample, a throat swab sample, a genital swab sample and an anal swab sample.

In some embodiments, the sample is a tissue sample such as a biopsy sample. The tissue sample may comprise cells indicative of a disease or condition. Exemplary diseases include cancers, such as bladder, breast, colorectal, kidney, lung, lymphoma, melanoma, oral or oropharyngeal, pancreatic, prostrate, thyroid, or uterine cancer.

In other embodiments, the sample may be an environmental sample from a source other than a subject. Suitably, the environmental sample may be a water sample such as from a drinking or cooking water source. Such drinking or cooking water sources include, without limitation, municipal water sources, wells, lakes, rivers, or reservoirs. In other embodiments, the environmental same may be a food sample or other consumable sample. In other embodiments, the environmental sample is a surface sample such as may be obtained from swabbing a surface.

Vessel

As used herein, a "vessel" is any container configured to contain a fluid or a dispersion. Suitably, the collection vessel may be a test tube, beaker, cup, jar, syringe, well in a plate, or other appropriate glassware or plastic wear.

Sample Lysate

As used herein, a "sample lysate" comprises the material formed by the lysis of cells, including nucleic acids and other biomolecules such as proteins, lipids, or carbohydrates. The sample lysate may further comprise one or more of the following: a lysis or denaturing agent, a nucleic acid preservation agent, a buffering agent, and a solvent. Combinations of a lysis or denaturing agent, a nucleic acid preservation agent, a buffering agent, and a solvent may be referred to as a "lysis buffer" or "lysis medium".

As used herein, a "lysis or denaturing agent" is a composition capable of breaking down or disrupting a cellular membrane. The lysis or denaturing agent may be a chaotropic salt, a lytic enzyme, a detergent, or any combination thereof. Suitably, the lysis or denaturing agent is present in an amount sufficient to break down or disrupt cellular membranes.

In some embodiments, the chaotropic salt is selected from guanidium thiocyanate, alkali metal perchlorates, alkali metal iodides, alkali metal trifluoroacetates, alkali metal trichloroacetates, and alkali metal thiocyanates. In some embodiments, the chaotropic salt is selected from urea, guanidine HCl, guanidinium thiocyanate, guanidium thiosulfate, thiourea, or any combination thereof. In some embodiments, the lysis or denaturing agent is a lytic enzyme.

In some embodiments, the lytic enzyme is selected from the group consisting of beta glucurondiase, glucanase, glusulase, lysozyme, lyticase, mannanase, mutanolysin, zymolase, cellulase, lysostaphin, pectolyase, streptolysin O, and various combinations thereof.

In some embodiments, the lysis or denaturing agent is a detergent. In some embodiments, the detergent is Tween. In some embodiments, the detergent is selected from 3-[(3-cholamidopropyl)dimethylammonio]-1-propanesulfonate, octyl-β-thioglucopyranoside, octyl-glucopyranoside, 3-(4-heptyl) phenyl 3-hydroxy propyl) dimethylammonio propane sulfonate, 3-[N,N-dimethyl(3-myristoylaminopropyl) ammonio]propanesulfonate, 3-(decyldimethylammonio) propanesulfonate inner salt, 3-(dodecyldimethylammonio) propanesulfonate inner salt, 3-(N,N-dimethylmyristylammonio)propanesulfonate, n-dodecyl α-D-maltoside and combinations thereof.

As used herein, a "nucleic acid preservation agent" is a composition capable of retarding the degradation of nucleic acids in the sample lysate. Nucleic acid preservation agents often act through the inhibition of nucleases. The nucleic acid preservation agent may be an enzyme inhibitor, a metabolic inhibitor, or any combination thereof. The one or more nucleic acid preservation agent may include a formaldehyde releaser such as one selected from the group consisting of: diazolidinyl urea, imidazolidinyl urea, dimethoylol-5,5-dimethylhydantoin, dimethylol urea, 2-bromo-2.-nitropropane-1,3-diol, oxazolidines, sodium hydroxymethyl glycinate, 5-hydroxymethoxymethyl-1-laza-3,7-dioxabicyclo [3.3.0]octane, 5-hydroxymethyl-1-laza-3,7dioxabicyclo[3.3.0]octane, 5-hydroxypoly[methyleneoxy] methyl-1-laza-3,7dioxabicyclo[3.3.0]octane, quaternary adamantine and any combination thereof. The one or more enzyme inhibitors may be selected from the group consisting of: diethyl pyrocarbonate, ethanol, aurintricarboxylic acid (ATA), glyceraldehydes, sodium fluoride, ethylenediamine tetraacetic acid (EDTA), formamide, vanadyl-ribonucleoside complexes, macaloid, heparin, hydroxylamine-oxygencupric ion, bentonite, ammonium sulfate, dithiothreitol (DTT), beta-mercaptoethanol, cysteine, dithioerythritol, tris (2-carboxyethyl)phosphene hydrochloride, a divalent cation such as $Mg^{+2}$, $Mn^{+2}$, $Zn^{+2}$, $Fe^{+2}$, $Ca^{+2}$, $Cu^{+2}$, and a chaotropic salt such as guanidinium thiocyanate, and any combination thereof. The one or more metabolic inhibitors may be selected from the group consisting of: glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof. Suitably, the nucleic acid preservation agent is present in an amount sufficient to retard the degradation of nucleic acids in the sample lysate.

Buffering agents may include one or more of the following: N-(2-acetamido)-aminoethanesulfonic acid; acetate; N-(2-acetamido)-iminodiacetic acid; 2-aminoethanesulfonic acid; ammonia; 2-amino-2-methyl-1-propanol; 2-amino-2-methyl-1,3-propanediol; N-(1,1-dimethyl-2-hydroxyethyl)-3-amino-2-hydroxypropanesulfonic acid; N,N-bis-(2-hydroxyethyl)-2-aminoethanesulfonic acid; carbonate; N,N'-bis(2-hydroxyethyl)-glycine; [bis-(2-hydroxyethyl)-imino]-tris-(hydroxymethylmethane); 1,3-bis[tris(hydroxymethyl)-methylamino]propane; boric acid; dimethylarsinic acid; 3-(cyclohexylamino)-propanesulfonic acid; 3-(cyclohexylamino)-2-hydroxy-1-propanesulfonic acid; cyclohexylaminoethanesulfonic acid; citrate; 3-[N-bis(hydroxyethyl) amino]-2-hydroxypropanesulfonic acid; formate; glycine; glycylglycine; N-(2-hydroxyethyl)-piperazine-N'-ethanesulfonic acid; N-(2-hydroxyethyl)-piperazine-N'-3-propanesulfonic acid; N-(2-hydroxyethyl)-piperazine-N'-2-hydroxypropanesulfonic acid; imidazole; malate; maleate; 2-(N-morpholino)-ethanesulfonic acid; 3-(N-morpholino)-propanesulfonic acid; 3-(N-morpholino)-2-hydroxypropanesulfonic acid; phosphate; piperazine-N,N'-bis(2-ethanesulfonic acid); piperazine-N,N'-bis(2-hydroxypropanesulfonic acid); pyridine; succinate; 3-{[tris (hydroxymethyl)-methyl]-amino}-propanesulfonic acid; 3-[N-tris(hydroxymethyl)-methylamino]-2-hydroxypropanesulfonic acid; triethanolamine; 2-[tris(hydroxymethyl)-methylamino]-ethanesulfonic acid; N-[tris(hydroxymethyl)-methyl]-glycine; and tris(hydroxymethyl)-aminomethane. The buffering agent may be added to the lysis medium as a salt comprising the buffering agent and a counter ion. Suitably, the buffering agent is present in an amount sufficient to maintain the acidity of a solution near the chosen value in the sample lysate.

The solvent may be any suitable solvent for the lysis or denaturing agent, a nucleic acid preservation agent, or a buffering agent. The solvent may be suitably selected from water.

In some embodiments of the invention, one or more compositions may perform the same function of a lysis or denaturing agent and a nucleic acid preservation agent, a lysis or denaturing agent and a buffering agent, or a nucleic acid preservation agent and a buffering agent. By way of example, guanidinium thiocyanate may be both a lysis or denaturing agent and a nuclear preservation agent because it can both break down or disrupt a cellular membrane and also denature a nuclease.

Suitably, the lysate sample has an ionic strength sufficiently high to allow for the formation of the salt bridges between the nucleic acids and the microspheres. The positively charged ions bridging the nucleic acids and the microspheres may be present as a result of the addition of a lysis or denaturing agent, a nucleic acid preservation agent, a the buffering agent, a salt thereof, or any combination thereof. The positively charged ion is selected from a monovalent ion such as $Na^+$ or $K^+$, a divalent cation such as $Mg^{+2}$, $Mn^{+2}$, $Zn^{+2}$, $Fe^{+2}$, $Ca^{+2}$, $Cu^{+2}$, or positively charged, nitrogen containing ion such as guanidinium. The positively charged ion may be present in a concentration greater than or equal to 1 M, 2M, 3M, or 4M.

Target Sequence

As used herein, a "target sequence" or "target nucleic acid sequence" is a nucleic acid sequence indicative of an origin or source. Suitably, the target sequence is indicative of the presence of a particular organism such as a pathogen. In other embodiments, the target sequence is indicative of the presence or absence of a disease or condition, such as the presence or absence of a genetic mutation associated with the disease or condition as may be the case with a cancer. In yet other embodiments, the target sequence is indicative of the prognosis, progression, or response to treatment for a disease or condition, such as the presence or absence of a genetic mutation or genetic marker associated with the prognosis, progression, or response to treatment for a disease or condition such as cancer. As used herein, "indicative" or "indicates" means to point to or be a sign of an origin or source, whether alone or in combination with additional target sequences or other information.

In some embodiments, the target nucleic acid sequence is a nucleic acid sequence from a eukaryotic source. In some embodiments, the eukaryotic source is selected from algae, protozoa, fungi, slime molds and/or mammalian cells.

In some embodiments, the target nucleic acid sequence is a nucleic acid sequence from a microorganism or virus. Suitably, the microorganism or virus may be *Escherichia, Campylobacter, Clostridium difficile,* Enterotoxigenic *E. coli* (ETEC), Enteroaggregative *E. coli* (EAggEC), Shiga-like Toxin producing *E. coli, Salmonella, Shigella, Vibrio cholera, Yersinia enterocolitica,* Adenovirus, Norovirus, Rotavirus A, *Cryptosporidium parvum, Entamoeba his-*

*tolytica, Giardia lamblia,* Clostridia, Methicillin-resistant *Staphylococcus aureus* MRSA, *Klebsiella pneumoniae* flu, Zika, dengue, chikungunya, West Nile virus, Japanese encephalitis, malaria, HIV, H1N1, and *Clostridium difficile* resistant organisms. In some embodiments, the target nucleic acid sequence is from a microorganism or virus selected from L DENV-1, DENV-2, DENV-3, DENV-4 RNA (dengue), tcdA and tcdB (*C. diff* toxin genes), ZIKV RNA (Zika), CHIKV RNA, (chikungunya), Giar-4, Giar-6 (*Giardia lamblia*), invasion antigen loci (ial), invasion plasmid antigen H (ipa H) (*Shigella*), GARV, VP7, NSP3 (rotavirus), and HuNoV (norovirus). In some embodiments, the pathogen is associated with sepsis such as Group B *Streptococcus* (GBS), *E. coli, Staphylococcus aureus*, Coagulase-negative *Staphylococcus* (CoNS), *Listeria monocytogenes, Enterococcus* sp, *Klebsiella* sp., and *Pseudomonas aeruginosa.*

In some embodiments, the target nucleic acid sequence is an rDNA or rRNA sequence from an organism. In some embodiments, the target nucleic acid sequence is an rRNA. In some embodiments, the rRNA is selected from 5 s, 16 s and 23 s rRNA. In some embodiments, the target nucleic acid sequence is selected from 5 s, 5.8 s, 28 s, and 18 s rRNA. In some embodiments, any embodiment listed herein is specifically excluded from the devices and methods disclosed herein.

In some embodiments, the target nucleic acid sequence is anywhere on the genome of a specific organism or virus that is specific to said organism or virus.

Washing Medium

As used herein, a "washing medium" is a substance capable of removing impurities adsorbed onto the surface of the microspheres or diluting residual lysate continuous phase associated with the particulate phase after separating the phases from one another. The washing medium should be selected such that nucleic acids adsorbed onto the surface of the microspheres are not extracted when the washing medium contacts the particulate phase. Suitably, the washing medium may be selected from water, an alcohol such as ethanol, medium salt buffer such as 100 mM or 200 mM NaCl, or combinations thereof.

Methods of Separating, Amplifying, and Detecting Nucleic Acids from a Sample

FIG. 1 illustrates a method of separating a nucleic acid from a sample. The method comprises contacting a sample lysate with a plurality of nucleic-acid-capture microspheres 4. As a result of the contact between a sample lysate and the microspheres, the nucleic acids are adsorbed or bound onto the surface of the microsphere and a lysate dispersion is formed. The lysate dispersion comprises a lysate continuous phase and a lysate particulate phase. The particulate phase comprises the plurality of microspheres and adsorbed nucleic acids obtained from the sample. The particulate phase comprises the sample lysate less the nucleic acids adsorbed to the microspheres, i.e., biomolecules other than adsorbed nucleic acids such as proteins, lipids, or carbohydrates, lysis or denaturing agents, nucleic acid preservation agents, buffering agents, or solvent that is not adsorbed onto the microspheres.

The method further comprises separating the lysate continuous phase from the particulate phase 6. Because the dispersion is unstable, the particulate phase with adsorbed nucleic acids spontaneously aggregates at the surface of continuous phase. The aggregation of the particulate phase allows for separation of the continuous phases. The separation may be accomplished, for example, by extracting the continuous phase, expelling the continuous phase, mechanically separating the continuous and particulate phases, or absorbing the particulate phase. Optionally the separation may employ a microsphere separation device such as a syringe, pipette, a microsphere-retaining mesh, a semi-permeable container, a absorption pad, or any combination thereof. Suitably at least some lysate continuous phase is separated from the particulate phase and, in some cases, a majority or substantially all of the lysate continuous phase is separated from the particulate phase.

The method also comprises contacting the particulate phase with an eluent 10. The eluent extracts the adsorbed nucleic acids from the surface of the microspheres, resulting in an eluate comprising nucleic acids obtained from the sample. Suitably the particulate phase is contacted with a sufficient amount of the eluent to extract nucleic acids bound onto the surface of the microspheres and, in some cases, a majority or substantially all of the nucleic acids bound onto the surface of the microspheres. In some embodiments, contacting the particulate phase with an eluent forms a eluate dispersion comprising a continuous phase and a particulate phase. The continuous phase of the eluate dispersion comprises the eluate and the particulate phase comprises the microspheres. The separation of the continuous and particulate phases may be accomplished by any method suitable for separating the continuous and particulate phases of a lysate dispersion, Such methods suitably include extracting the continuous phase, expelling the continuous phase, mechanically separating the continuous and particulate phases, or absorbing the particulate phase.

The entire nucleic acid separation protocol may be finished within 20 minutes without using any professional laboratory instrumentation such as centrifuges or refrigeration.

The method may further comprise washing the particulate phase 8 prior to contacting the particulate phase with an eluent 10. Washing the particulate phase may comprise contacting the particulate phase with a washing medium to form a washing dispersion and separating the continuous and particulate phases of the washing dispersion. The washing medium should be selected to remove impurities more weakly adsorbed onto the surface of the microspheres than the adsorbed nucleic acids without extracting substantially all of the nucleic acids or dilute any residual lysate continuous phase associated with the particulate phase. Suitably the particulate phase is contacted with a sufficient amount of the washing medium to move some or all of the impurities adsorbed onto the surface of the microspheres or to dilute any residual lysate continuous phase associated with the particulate phase. The separation of the continuous and particulate phases may be accomplished by any method suitable for separating the continuous and particulate phases of a lysate dispersion, Such methods suitably include extracting the continuous phase, expelling the continuous phase, mechanically separating the continuous and particulate phases, or absorbing the particulate phase.

The method may further comprise providing a sample 2. Providing the same may comprise contacting a sample with a lysis or denaturing agent to prepare the sample lysate. Suitably the sample may be contacted with a lysis medium comprising the lysis medium comprising the lysis or denaturing agent.

Another aspect of the invention is a method for amplifying a nucleic acid obtained from a sample. The method comprises separating nucleic acids from a sample as described above and further comprising amplifying the nucleic acid separated from the sample 12.

Figure 2A:
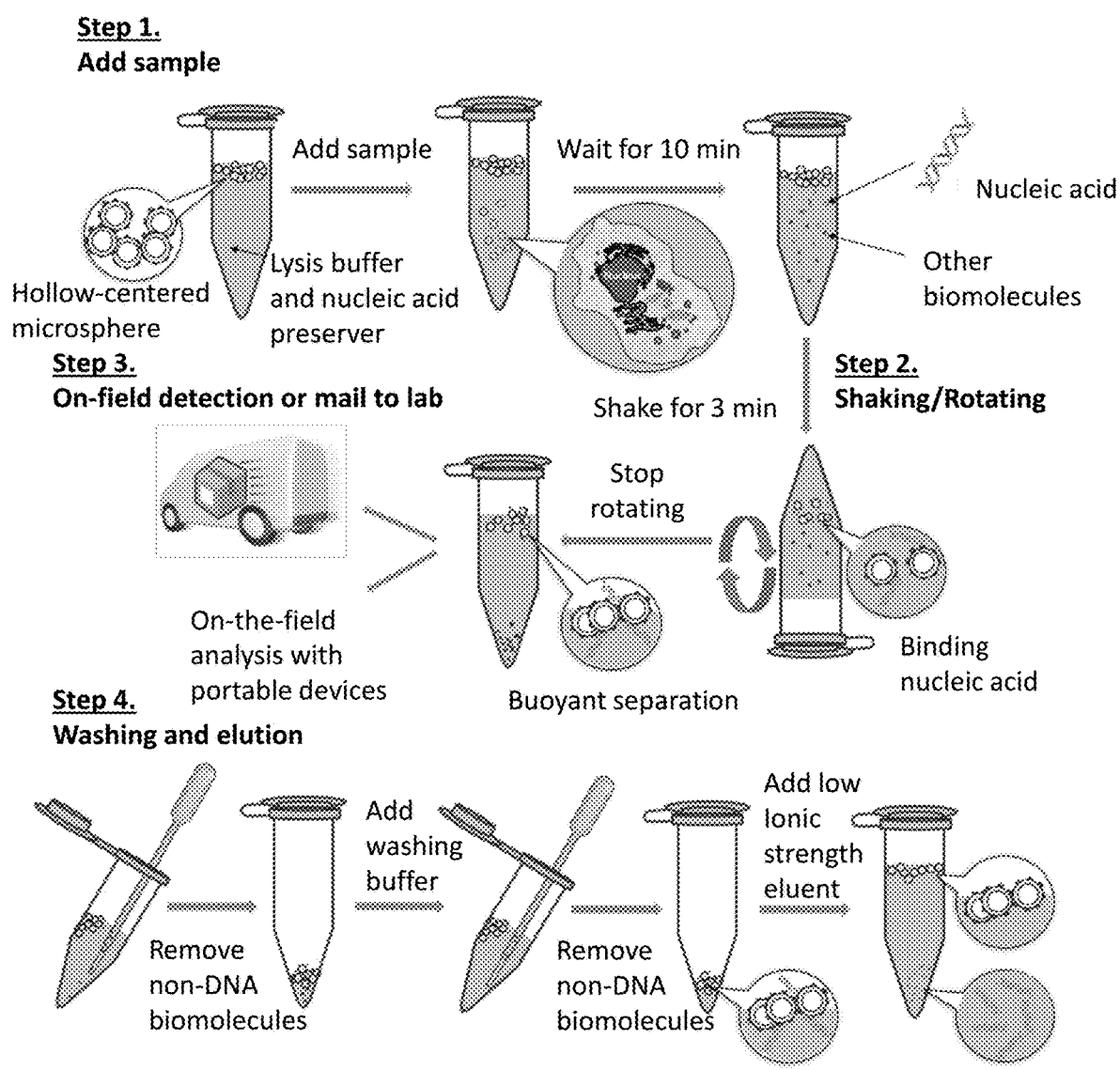
FIG. 2A schematically illustrates the use of microspheres for the separation of nucleic acids by extracting the lysate continuous phase.

Exemplary methods for separating, amplifying, and detecting nucleic acids are illustrated in FIGS. 2A-2D. FIG. 2A illustrates an exemplary method that separates the continuous and particulate phases for both the lysate dispersion as well as a washing dispersion. As shown, the method comprises providing the sample lysate. Preparation of the sample lysate is accomplished by adding microspheres and a lysis medium to a sample collection vessel. A sample comprising cells is added to the sample collection vessel. Although FIG. 2A illustrates the addition of the microspheres and the lysis medium to the sample collection vessel prior to the addition of the sample, the microspheres, lysis medium, and sample may be added to the sample collection vessel in any order. The sample is allowed to incubate with the lysis medium comprising a sufficient amount of a lysis or denaturing agent for a sufficient amount of time to result in the break down or disruption of cellular membranes. This in turn releases nucleic acids from the cell into the continuous phase of a sample lysate, preparing a cellular lysate comprising the nucleic acids and other biomolecules. As shown in FIG. 2A, the microspheres are present in the sample collection vessel when the sample is incubated with the lysis medium, however the microspheres may be added following the break down or disruption of cellular membranes. The microspheres are allowed to contact the sample lysate thereby causing at least some of the nucleic acids to absorb onto the surface of the microspheres.

FIG. 2A illustrates that the absorption process can be facilitated or accelerated by shaking, rotating, inverting, or otherwise manipulating the sample collection vessel and the contents therein to improve mass transfer. Although such a step may accelerate the absorption of nucleic acids onto the surface of the microsphere, such a step is not necessary provided that the microspheres and the sample lysate are in contact for a sufficient amount of time. After the conclusion of the manipulating the sample collection vessel and the contents therein, the dispersion formed of the microspheres and sample lysate will spontaneously separate. The particulate phase comprising the plurality of buoyant, inorganic, nucleic-acid-capture microspheres and an adsorbed nucleic acid obtained from the sample will aggregate at the surface of the dispersion, while the continuous phase comprising a nucleic acid depleted continuous phase will settle to the bottom of the sample collection vessel. The sample collection vessel comprising the dispersion may be stored, transported to a laboratory for further processing or testing, or undergo further on-site processing or testing.

As also shown in FIG. 2A, the continuous phase may be extracted after the spontaneous aggregation of the particulate phase from the continuous phase. As used herein, "extracting" means removing the continuous phase from the vessel. The continuous phase may be extracted under vacuum by a microsphere separating device configured to generate a vacuum, such as a dropper, pipette, syringe, or other suitable instrument or device. The microsphere separating device may comprise a microsphere-retaining mesh positioned to prevent some or all of the microspheres from being extracted with the continuous. For example, a dropper, pipette, or syringe may comprise a microsphere-retaining mesh positioned to prevent the particulate phase from being drawn into a tip of the pipette, a tip of the syringe, or a tip of the dropper. Following extraction of the continuous phase, the particulate phase remaining in the vessel may undergo washing with a suitable washing medium to dilute any residual continuous phase remaining in the vessel and/or desorbs substances adsorbed onto the surface of the microsphere other than the nucleic acids. The washing step may result in the creation of a washing dispersion comprising a washing particulate phase comprising the microspheres and nucleic acids adsorbed thereon and a washing continuous phase comprising the washing medium. The washing particulate phase and the washing continuous phase may be separated by any suitable method, e.g., by extracting the washing continuous phase as shown in FIG. 2A. The washing step may be repeated one or more times or be omitted.

Finally, FIG. 2A illustrates the addition of an eluent to the vessel to extract the nucleic acids from the surface of the microspheres. Following the addition of the eluent, an elution dispersion is formed. The elution dispersion comprising a particulate phase having microspheres and a continuous phase of the eluate and nucleic acids extracted from the microspheres therein. The eluate may be separated from the particulate phase by any suitable method, e.g., by extracting the washing continuous phase. The eluate may be stored, transported to a laboratory for further processing or testing, or undergo further on-site processing or testing such as nucleic acid amplification or testing with a lateral flow device.

Figure 2B:
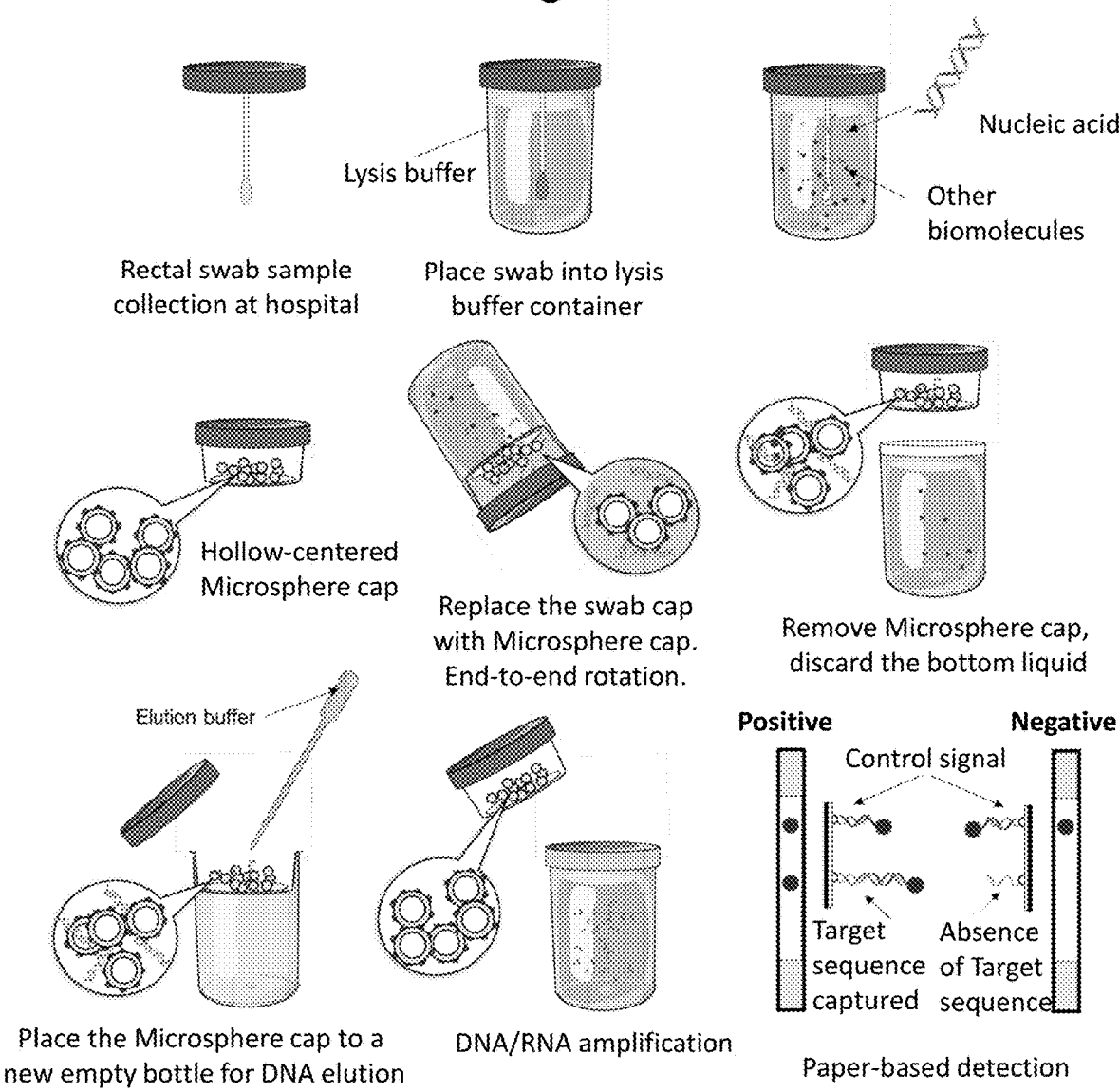
FIG. 2B schematically illustrates the use of microspheres for the separation of nucleic acids by mechanically separating the lysate particulate phase.

FIG. 2B illustrates another exemplary method that separates the continuous and particulate phases for both the lysate dispersion as well as an elution dispersion. As shown, the method comprises providing the sample lysate. Preparation of the sample lysate is accomplished by adding a swab, e.g., a rectal swab, having a sample, such as stool, disposed thereon that has been collected from a subject and a lysis medium to a sample collection vessel. The swab comprising the sample is allowed to incubate with the lysis medium comprising a sufficient amount of a lysis or denaturing agent for a sufficient amount of time to result in the break down or disruption of cellular membranes. This in turn releases nucleic acids from the cell into the continuous phase of a sample lysate, preparing a cellular lysate comprising the nucleic acids and other biomolecules.

As shown in FIG. 2B, the swab may be removed from the sample collection vessel and the microspheres may be added. The microspheres may be added with use of microsphere-separation device such as semi-permeable container having the microspheres therein, such as a microsphere cap as shown in FIG. 2B. Alternatively, the microspheres may be added directly to the sample collection vessel. The microspheres are allowed to contact the sample lysate thereby causing at least some of the nucleic acids to absorb onto the surface of the microspheres. FIG. 2B illustrates that the absorption process can be facilitated or accelerated by shaking, rotating, inverting, or otherwise manipulating the sample collection vessel and the contents therein to improve mass transfer. Although such a step may accelerate the absorption of nucleic acids onto the surface of the microsphere, such a step is not necessary provided that the microspheres and the sample lysate are in contact for a sufficient amount of time. After the conclusion of the manipulating the sample collection vessel and the contents therein, the dispersion formed of the microspheres and sample lysate will spontaneously separate. The spontaneous separation may be limited if a semi-permeable container is used. The particulate phase comprising the plurality of buoyant, inorganic, nucleic-acid-capture microspheres and an adsorbed nucleic acid obtained from the sample will aggregate at the surface of the dispersion, while the continuous phase comprising a nucleic acid depleted continuous phase will settle to the bottom of the sample collection vessel. The sample collection vessel comprising the dispersion may be stored, transported to a laboratory for further processing or testing, or undergo further on-site processing or testing.

As also shown in FIG. 2B, the particulate phase may be mechanically separated. The particulate phase may be mechanically separated with the use of a microsphere separating device such as the semi-permeable container shown in FIG. 2B. Following mechanical separation of the particulate phase, the continuous phase remaining in the vessel may be discarded. The microspheres may be returned to the same sample collection vessel or a different washing vessel or nucleic acid collection vessel.

FIG. 2B also illustrates an eluent contacting the microspheres to extract the nucleic acids. Following the addition of the eluent, an eluate comprising the extracted nucleic acids drains through the semi-permeable container into a nucleic acid collection vessel. The eluate may be separated from the particulate phase by any suitable method, e.g., by mechanically separating the microspheres by removing the semi-permeable container. The eluate may be stored, transported to a laboratory for further processing or testing, or undergo further on-site processing or testing such as nucleic acid amplification or testing with a lateral flow device, which are both illustrated in FIG. 2B.

FIG. 2B does not illustrate a separate washing step. In some instances, the eluent may perform some of the functions of a washing medium, such as dilution of residual continuous phase associated with the microspheres.

Figure 2C:
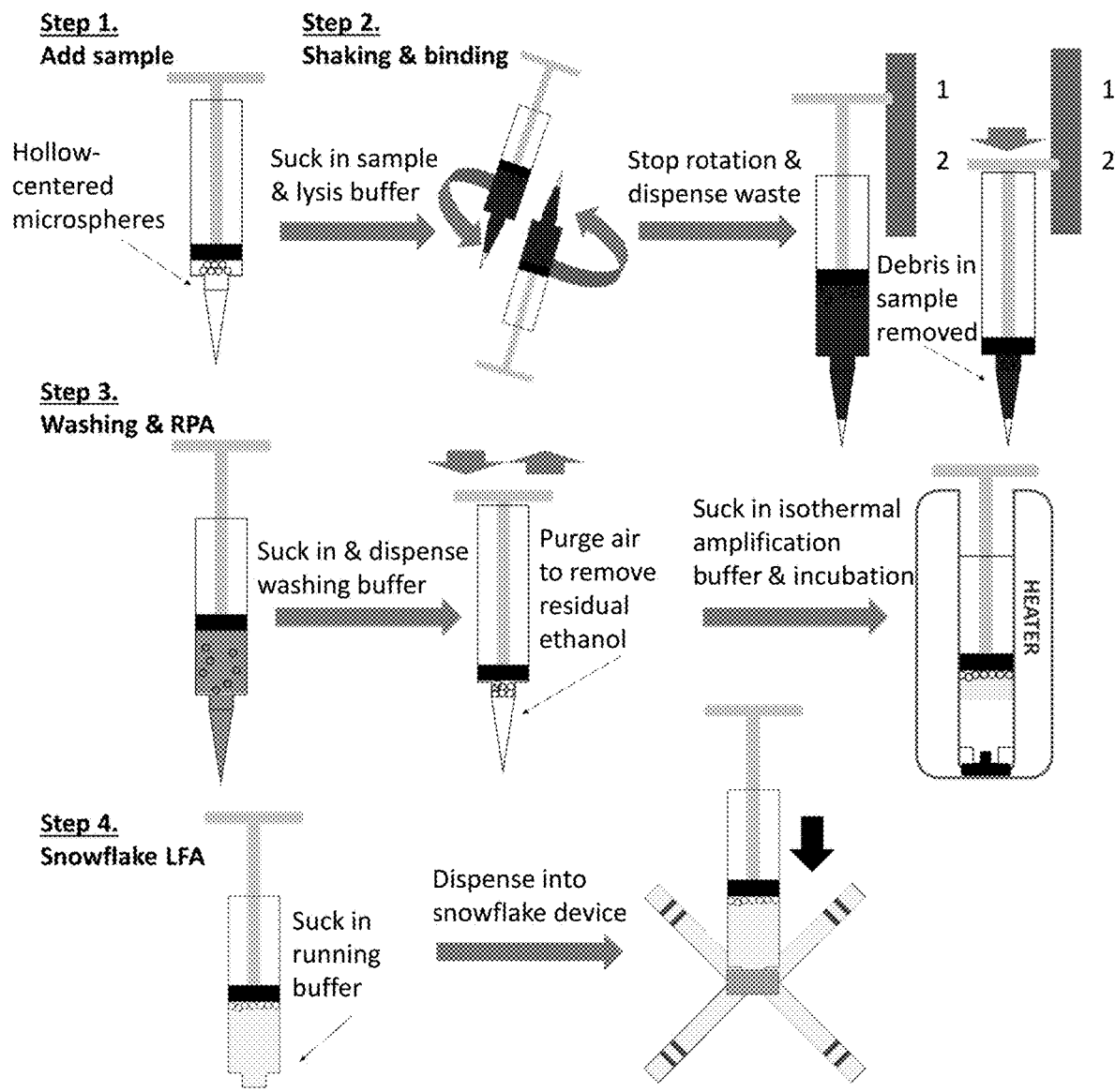
FIG. 2C schematically illustrates the use of microspheres for the separation of nucleic acids by expelling the lysate continuous phase.

FIG. 2C illustrates another exemplary method that separates the continuous and particulate phases for each of a lysate dispersion, a washing dispersion, and an amplification dispersion by expelling the continuous phase. As shown, the method comprises providing the sample lysate. Preparation of the sample lysate is accomplished by adding a sample and a lysis medium to a sample collection vessel, which is also a microsphere separating device, preloaded with microspheres. Although The sample is allowed to incubate with the lysis medium comprising a sufficient amount of a lysis or denaturing agent for a sufficient amount of time to result in the break down or disruption of cellular membranes. This in turn releases nucleic acids from the cell into the continuous phase of a sample lysate, preparing a cellular lysate comprising the nucleic acids and other biomolecules.

FIG. 2C illustrates that the absorption process can be facilitated or accelerated by shaking, rotating, inverting, or otherwise manipulating the sample collection vessel and the contents therein to improve mass transfer. Although such a step may accelerate the absorption of nucleic acids onto the surface of the microsphere, such a step is not necessary provided that the microspheres and the sample lysate are in contact for a sufficient amount of time. After the conclusion of the manipulating the sample collection vessel and the contents therein, the dispersion formed of the microspheres and sample lysate will spontaneously separate. The particulate phase comprising the plurality of buoyant, inorganic, nucleic-acid-capture microspheres and an adsorbed nucleic acid obtained from the sample will aggregate at the surface of the dispersion, while the continuous phase comprising a nucleic acid depleted continuous phase will settle to the bottom of the sample collection vessel. The sample collection vessel comprising the dispersion may be stored, transported to a laboratory for further processing or testing, or undergo further on-site processing or testing.

As also shown in FIG. 2C, the continuous phase may be expelled after the spontaneous aggregation of the particulate phase from the continuous phase. The continuous phase may be expelled under pressure by a microsphere separating device configured to generate a pressure, such as a dropper, pipette, syringe, or other suitable instrument or device. The microsphere separating device may comprise a microsphere-retaining mesh positioned to prevent some or all of the microspheres from being expelled with the continuous phase. For example, a dropper, pipette, or syringe may comprise a microsphere-retaining mesh positioned to prevent the particulate phase from being expelled from a tip of the pipette, a tip of the syringe, or a tip of the dropper.

Following expulsion of the continuous phase, the particulate phase remaining in the vessel may undergo washing with a suitable washing medium to dilute any residual continuous phase remaining in the vessel and/or desorbs substances adsorbed onto the surface of the microsphere other than the nucleic acids. The washing step may be accomplished by drawing washing medium into the vessel under vacuum. The washing step may result in the creation of a washing dispersion comprising a washing particulate phase comprising the microspheres and nucleic acids adsorbed thereon and a washing continuous phase comprising the washing medium. The washing particulate phase and the washing continuous phase may be separated by any suitable method, e.g., by expelling the washing continuous phase as shown in FIG. 2C. The washing step may be repeated one or more times or be omitted.

FIG. 2C also illustrates that an amplification medium may be drawn into the vessel comprising the microspheres having nucleic acids adsorbed thereon. Notably, the amplification medium may be configured perform the same function as an eluent and cause nucleic acids to be extracted from the surface of the microspheres. The vessel may than be heated under suitable conditions to amplify a target sequence, if present.

Subsequent to amplification, the amplification dispersion comprising a particulate phase and an amplification continuous phase may be separated by any suitable method, such as by expelling the amplification continuous phase as shown in FIG. 2C. The expelled amplification phase comprises the amplicons prepared by amplification, and the amplicons may then be subjected to a testing methods to determine the present or absence of a target sequence. Suitably, the amplicons may be detected by expelling the continuous phase onto the sample loading area of a lateral flow device, such as the multiplexed, or "snow flake" lateral flow device illustrated in FIG. 2C.

Figure 2D:
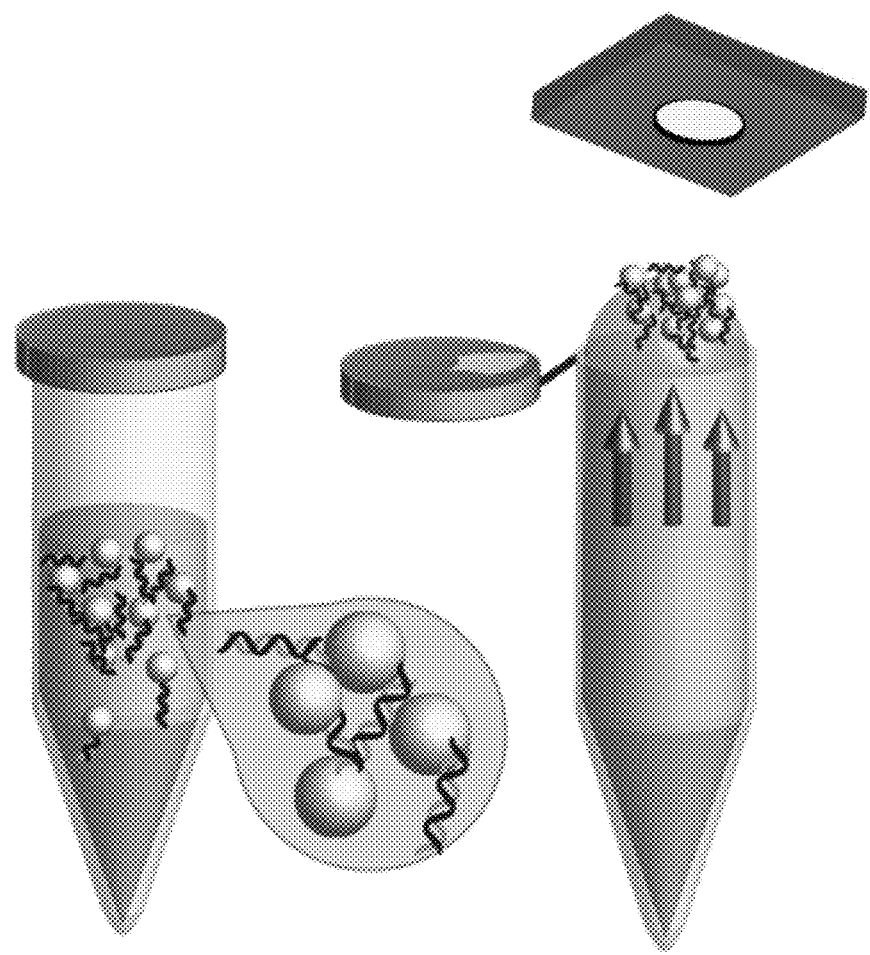
FIG. 2D schematically illustrates the use of microspheres for the separation of nucleic acids by absorbing the lysate particulate phase.

Yet another separation method is illustrated in FIG. 2D. FIG. 2D illustrates the separation of the particulate phase by absorption of the particulate phase of a lysate dispersion onto an absorption pad. Suitably the absorption pad is a microsphere loading pad. The lysate dispersion in a sample collection vessel can augmented, such as with a washing medium, to increase the volume of the continuous phase. As the volume of the continuous phase, the aggregated particulate phase will rise with the rising level of the surface of the continuous phase. A sufficient amount of augmentation, a convex meniscus may form and rise above the top of the vessel. The microspheres within the meniscus may be adsorbed onto the absorption pad by dabbing the absorption pad onto the meniscus, separating the particulate phase and nucleic acids adsorbed thereon from the continuous phase.

Kits for Separating, Amplifying, and Detecting Nucleic Acids

Another aspect of the invention comprises a kit comprising a plurality of buoyant, inorganic, nucleic-acid-capture microspheres. The kit may comprises one or more of the following: a eluent; a lysis medium, a lysis or denaturing agent; a washing medium; an amplification medium; a swab;

a sample collection vessel; a microsphere separation device; a nucleic acid collection vessel; an amplification device; a testing device; and a control nucleic acid. The kit may be used to perform any of the methods described herein.

In some embodiments, the kits are suitable for use in separating nucleic acids from a sample. Suitably the kit comprises a plurality of buoyant, inorganic, nucleic-acid-capture microspheres and one or more of the following: a eluent; a lysis medium, a lysis or denaturing agent; a washing medium; a swab; a sample collection vessel; a microsphere separation device; and a nucleic acid collection vessel. In certain embodiments, the kit comprises a plurality of buoyant, inorganic, nucleic-acid-capture microspheres and a microsphere separation device. The microsphere separation device may be suitably selected from any of the microsphere separation devices described herein.

In some embodiments, the kits are suitable for use in amplifying nucleic acids from a sample. Suitably the kit may comprises one or more of the following: a eluent; a lysis medium, a lysis or denaturing agent; a washing medium; an amplification medium; a swab; a sample collection vessel; a microsphere separation device; a nucleic acid collection vessel; and an amplification device. In certain embodiments, the kit comprises a plurality of buoyant, inorganic, nucleic-acid-capture microspheres and a microsphere separation device. The microsphere separation device may be suitably selected from any of the microsphere separation devices described herein.

In some embodiments, the kits are suitable for use in detecting nucleic acids from a sample. Suitably the kit may comprises one or more of the following: a eluent; a lysis medium, a lysis or denaturing agent; a washing medium; an amplification medium; a swab; a sample collection vessel; a microsphere separation device; a nucleic acid collection vessel; an amplification device, a testing device; and a control nucleic acid. In certain embodiments, the kit comprises a plurality of buoyant, inorganic, nucleic-acid-capture microspheres and a microsphere separation device. The microsphere separation device may be suitably selected from any of the microsphere separation devices described herein.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1: Binding Fluorescently Labeled Oligonucleotides to Hollow Microspheres Biotinylated oligonucleotides (100 nM) were conjugated with an excess amount of streptavidin tagged Alexa Fluoro 488 dye, providing fluorescently labeled oligonucleotides. The fluorescently labeled nucleotides were added to a vessel containing XLD3000 hollow microspheres in the presence of a lysis medium comprising 4M guanidinium isothiocyanate and allowed to incubate for 10 minutes. Bright-field and epi-fluorescence images where taken. Overlaying the images reveals that the fluorescent nucleotides were bound to the surface of microspheres, providing a bright green signal that was co-localized with the surface of the hollow microspheres (FIG. 3B). As a control, bright-field and epi-fluorescence images were obtained for microspheres without oligonucleotides present. In contrast, the control sample failed to demonstrate fluorescence, resulting in a gray image of the hollow microspheres (FIG. 3A). The images confirm that the hollow microspheres bind the target oligonucleotides onto the sphere surface.

Example 2: Detection of *E. coli* Bacteria in a Spiked Urine Sample with a Lateral Flow Test Strip FIG. 4 exemplifies integration of microsphere nucleic acid separation and gold nanoparticle colorimetric lateral flow diagnostic detection to detect *E. coli* bacteria from urine sample. After the microsphere separation, the *E. coli* containing samples were tested via paper strip with a positive signal. As shown in FIG. 4, both of the lateral flow strip tests of the human urine sample with and without *E. coli* bacteria spike-in have the control dot signal, which indicated the assay is functional. The sample that spike-in with the *E. coli* bacteria has the test positive signal means the *E. coli* bacteria DNA has been separated by microsphere separation method and detected by the lateral flow assay.

Example 3: Detection of *Cryptosporidium* Oocysts

Figure 5:
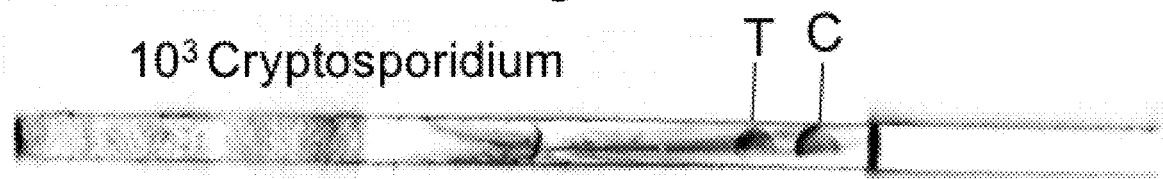
FIG. 5 shows paper strips in which *Cryptosporidium* oocysts ($1 \times 10^3$ cells) are lysed and purified using hollow microspheres prior to application on paper.

FIG. 5 exemplifies integration of microsphere nucleic acid separation and gold nanoparticle colorimetric lateral flow diagnostic detection to detect *Cryptosporidium* oocysts. After the microsphere separation, the $10^3$ *Cryptosporidium* containing samples were tested via paper strip with a positive signal. The limited detection of the paper diagnostics were improved by the separation.

Example 4: *C. diff* Genomic DNA Amplification

The limit of amplification and detection of *C. diff* genomic DNA via LAMP was tested by titrating *C. diff* genomic DNA and then amplifying by LAMP assay. *C. diff* genomic DNA was obtained American Type Culture Collection (ATCC) (Manassas, Va.). The DNA, at concentrations of 0.1 ng, 0.5 ng, 1 ng, 5, ng, 10 ng, 50 ng, and 100 ng, was amplified by LAMP using the primers listed in Table 4. The LAMP reaction also used the LAMP master mix reagents, including DNA polymerase buffer, Tris-HCl, $(NH_4)_2SO_4$, KCl, $MgSO_4$, Tween 20, dNTPs (100 mM), Betaine (5 M), designed primers, Bst DNA polymerase, and nuclease free water as shown in Table 5.

Figure 6:
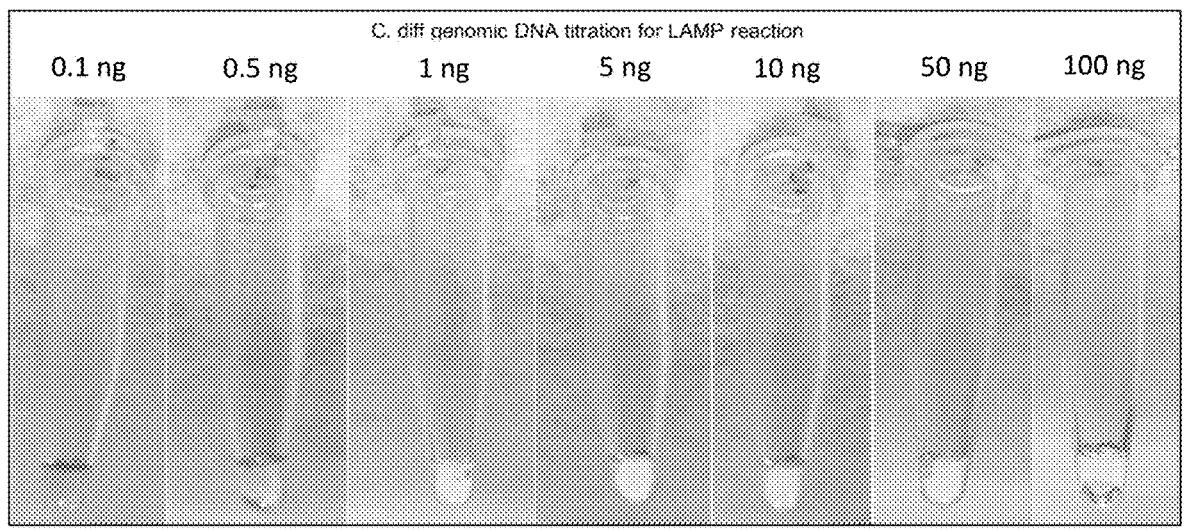
FIG. 6 shows the limit of detection test of *C. diff* genomic DNA via LAMP amplification.

After the reaction, the amplification results were characterized by adding 100× SYBR green dye and visually identifying green emission, as shown in FIG. 6. The fluorescent data reveals that the limit of LAMP amplification was between 0.5 ng and 1 ng, which means around 2,000 target DNA per 1 ml sample can be amplified and detected via this LAMP method. As a result, detection of femtomolar concentrations of DNA in a sample using lateral flow devices is possible. In contrast, only nanomolar concentrations of DNA may be detected without amplification.

TABLE 4

LAMP primers sequences

| Oligo Name | 5' Mod | Sequence |
|---|---|---|
| *E. coli* | | |
| E-F3 | | GCCATCTCCTGATGACGC (SEQ ID NO: 25) |
| E-B3 | | ATTTACCGCAGCCAGACG (SEQ ID NO: 26) |
| E-BIP | | CTGGGGCGAGGTCGTGGTATTCCGACAAACACCACGAATT (SEQ ID NO: 27) |
| E-FIP | | CATTTTGCAGCTGTACGCTCGCAGCCCATCATGAATGTTGCT (SEQ ID NO: 28) |
| E-LF | | CTTTGTAACAACCTGTCATCGACA (SEQ ID NO: 29) |
| E-LB | | ATCAATCTCGATATCCATGAAGGTG (SEQ ID NO: 30) |
| *C. diff* | | |
| CD-F3 | | GTATCAACTGCATTAGATGAAAC (SEQ ID NO: 31) |
| CD-B3 | | CCAAAGATGAAGTAATGATTGC (SEQ ID NO: 32) |
| CD-FIB | | CTGCACCTAAACTTACACCATCTATCTTCCTACATTATCTGAAGGATT (SEQ ID NO: 33) |
| CD-BIP | | GAGCTAAGTGAAACGAGTGACCCGCTGTTGTTAAATTTACTGCC (SEQ ID NO: 34) |
| CD-FL-FAM | [6FAM] | AATAGTTGCAATTATAGG (SEQ ID NO: 35) |
| CD-BL-BIO | [Btn] | AGACAAGAAATAGAAGCTAAGATAGG (SEQ ID NO: 36) |
| EPEC | | |
| EPEC-F3 | | CGACGATTTGGTCGTTGAA (SEQ ID NO: 41) |
| EPEC-B3 | | TGTCATCGGTCATGTTGC (SEQ ID NO: 42) |
| EPEC-FIP-FAM | [6FAM] | CAAAATGATCTGCTGACCAGGCTTTTTAAGCATTTATACAGTTCTGAAAGC (SEQ ID NO: 43) |
| EPEC-BIP-BIO | [Btn] | ACAGTGCACTACCACTTTTAGGTTTTTCATTTTAGTCAGTTTATTCGTGTGA (SEQ ID NO: 44) |

TABLE 5

LAMP Amplification Medium

| Amplification reagents | Final Conc. |
|---|---|
| Bst DNA polymerase buffer | 10x |
| Tris-HCl (pH 8.8) | 20 mM |
| $(NH_4)_2SO_4$ | 10 mM |
| KCl | 10 mM |
| $MgSO_4$ | 2 mM |
| Tween 20 | 0.10% |
| dNTPs (100 mM) | 1 mM |
| Betaine (5M) | 200 mM |
| F3 primer (10 pmol/μL) | 7.5 pmol |
| B3 primer (10 pmol/μL) | 7.5 pmol |
| FIP primer (10 pmol/μL) | 75 pmol |
| BIP primer (10 pmol/μL) | 75 pmol |
| LF primer (10 pmol/μL) | 30 pmol |
| LB primer (10 pmol/μL) | 30 pmol |
| Bst DNA polymerase | 8 U |
| $H_2O$ | q.s. |
| MM total | 23 ul |

Example 5: *C. diff* Genomic DNA Following Microsphere Separation

DNA amplification following microsphere separation was evaluated. Three samples were prepared: a negative control comprising water, a positive control comprising PBS solution spiked with *C. diff* genomic DNA; and a sample comprising microsphere separated *C. diff* genomic DNA from a DNA spike-in PBS solution. The samples where amplified under suitable conditions with the primers listed in Table 4.

Figure 7:
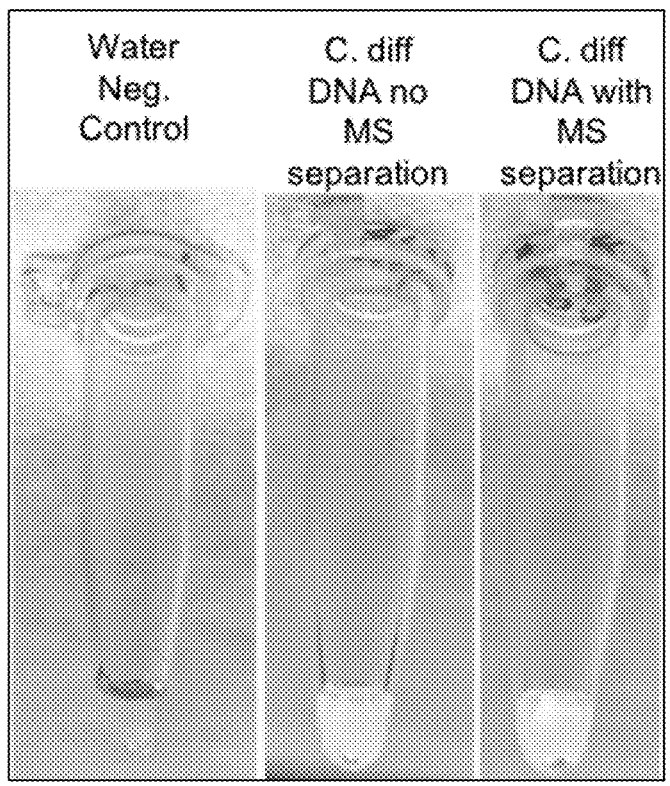
FIG. 7 shows the effective microsphere separation and amplification of *C. diff* DNA.

FIG. 7 demonstrates that *C. diff* genomic DNA may be amplified following microsphere separation. The negative control sample has no fluorescence signal, indicating that the LAMP primers were specific for the *C. diff* DNA target sequence. The positive control displays a strong fluorescence signal. The microsphere separated sample also shows a strong fluorescence signal with similar intensity compare to the positive control. These results show that the microsphere sample preparation assay efficiently isolates and releases DNA, and the reagents and solvents used for the separation do not inhibit the amplification reaction.

Example 6: *E. coli* Genomic DNA Amplification

Figure 8:
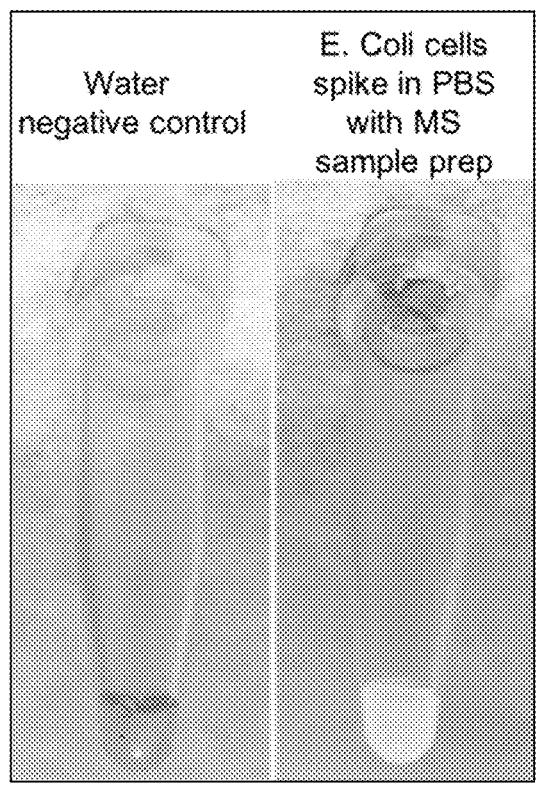
FIG. 8 shows the effective microsphere separation and amplification of *E. coli* DNA.

The microsphere separation of *E. coli* DNA from bacterial cells followed by amplification by LAMP was also examined. *E. coli* bacterial cells were first lysed by 4M Guanidinium isothiocyanate and incubated with 3 mg microspheres. The *E. coli* DNA lysates were captured and then separated by microspheres. The microsphere-DNA complexes were then transferred to wax-printed chromatography papers and washed with 100 μL 70% ethanol. After washing, the isolated DNAs were eluted by adding 100 μL water. Next, 2 μL out of 100 μL DNA eluates were amplified via LAMP reaction for 40 min using the primers and LAMP reaction master mix provided in Tables 4 and 5, respectively. 2 μL amplicons were added to clear microfuge tubes along with 10 μL 100× SYBR green fluorescent dye. Fluorescence was visually identified, as shown in FIG. 8. The results demonstrate that bacteria cells may be successfully lysed, their nucleic acids isolated with hollow microspheres and released from the microspheres, and that the isolated nucleic acids in the eluate may be effectively amplified.

Example 7: *E. coli* Genomic DNA Amplification in Blood Sample

*E. coli* DNA spiked blood samples were tested to establish that the DNA may be effectively amplified and detected in the complex sample.

Figure 9:
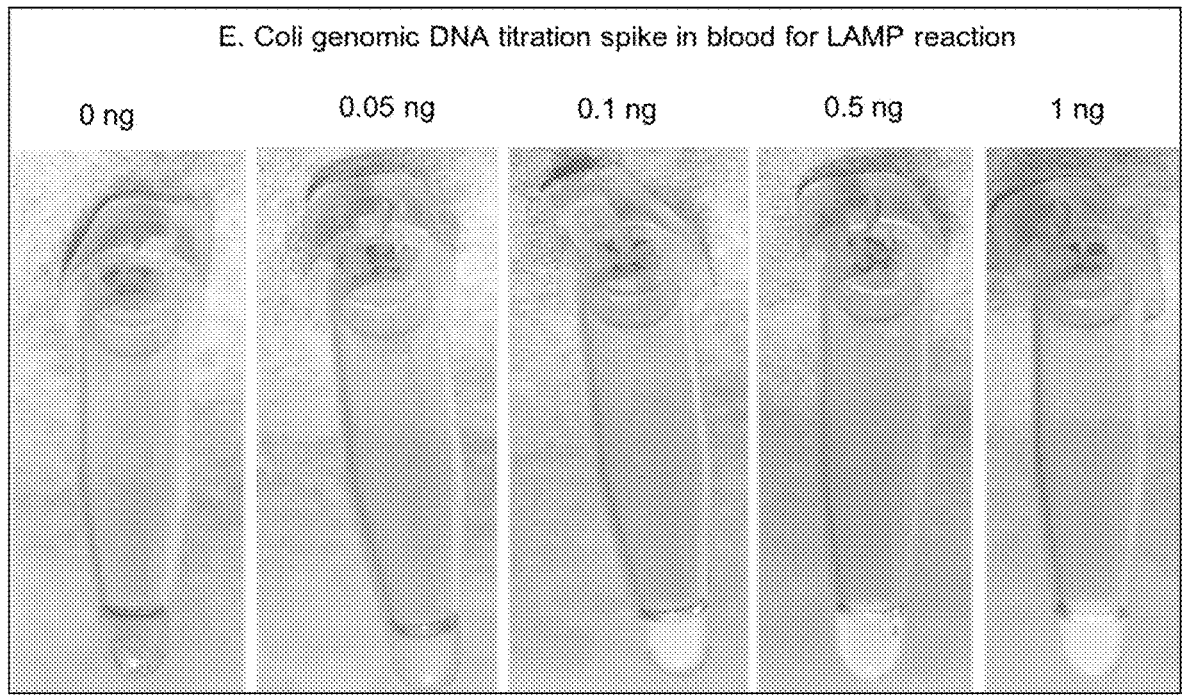
FIG. 9 shows the effective microsphere separation and amplification of *E. coli* DNA from a blood sample.

A piece of glass fiber was stuck onto a microfuge tube opening for each sample. The DNA spike in blood samples were then transferred onto the glass fiber, and the DNA gradually filtered down to the microfuge tube under the glass fiber by gravity. The blood DNA filtrates were then amplified by LAMP. The results, shown in FIG. 9, demonstrate that the limit of LAMP amplification of DNA in blood was between 0.05 ng and 0.1 ng, which was very close to the limit of detection in PBS buffer.

Example 8: Microsphere Separation and Detection of *C. diff*. Genomic DNA

Figure 10:
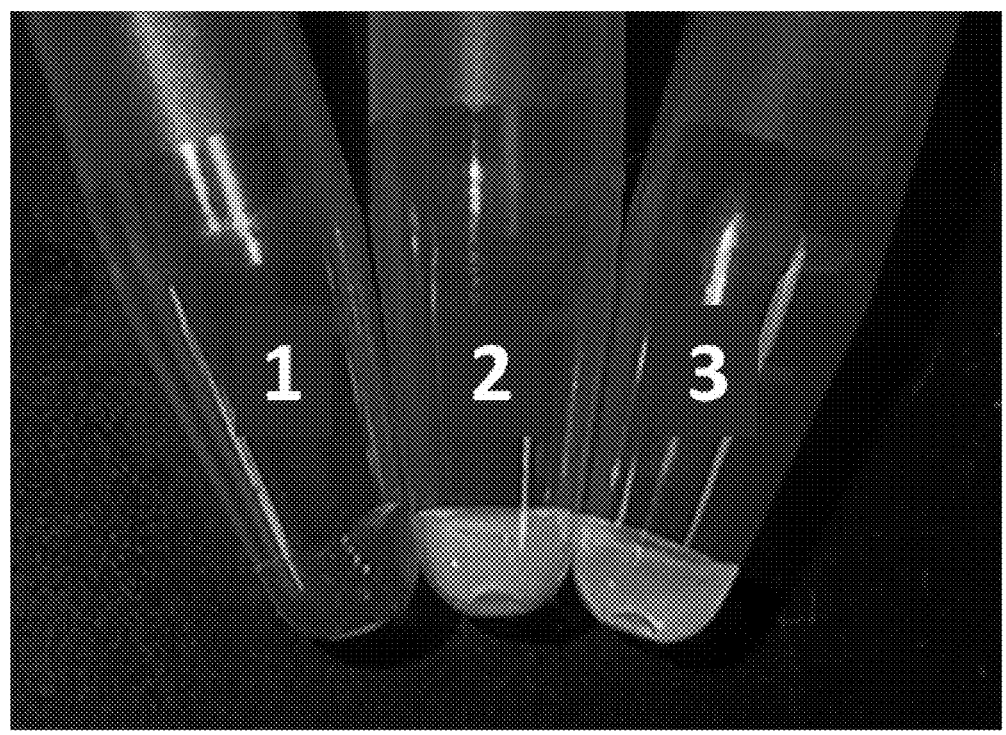
FIG. 10 shows *C. diff* genomic DNA extraction, amplification, and detection. Tube 1 (dark): a negative control using water as sample for LAMP. Tube 2 (green): LAMP detection of genomic DNA extracted using a syringe and microspheres. Tube 3 (green): LAMP detection of genomic DNA extracted using microspheres in microcentrifuge tube and pipettes.

To demonstrate the use of microspheres in a syringe for nucleic acid extraction, 160 ng genomic DNA from *Clostridioides difficile* (ATCC Manassas, Va., USA) was added to 500 μL lysis buffer (4 M guanidine thiocyanate, MilliporeSigma, Burlington, Mass., USA) in a 1.5 ml centrifuge tube. The mixed buffer was then sucked into a BD Luer-Lok™ 1-mL syringe (Becton, Dickinson and Company, Franklin Lakes, N.J., USA) through a plastic tapered needle with microspheres pre-loaded. The genomic DNA was then extracted from the lysis buffer following the scheme shown in FIG. 2C, washed with 80% ethanol once and eluted with 100 μL nuclease-free water. For comparison, another tube of 500 μL lysis buffer and 160 ng genomic DNA was mixed and processed following the microsphere nucleic acid extraction protocol in tube using pipettes but without the syringe. After the elution, 2 μL of eluate derived from each protocols was tested using a LAMP specific for the tcdB gene of *Clostridioides difficile*. Each 25 μL of LAMP buffer contains 2.5 μL of 10× isothermal amplification buffer, 1.4 mM dNTPs, 6 mM $MgSO_4$, 2.5 μL of 10× primer mix, 8 U Bst 2.0 WarmStart® DNA Polymerase. All reagents in the LAMP system were obtained from New England Biolabs (Ipswich, Mass., USA). The primer mix contains 1.6 μM FIP/BIP primers, 0.2 μM F3/B3 primers, and 0.4 μM LF/LB primers obtained from Integrated DNA Technology (Skokie, Ill., USA). LAMP was conducted by incubating the mixture at 65° C. for 30 minutes using a heat block. The amplification was evaluated by mixing the amplicons with a SYBR Green I gel stain and observing the fluorescence of the SYBR-DNA complex under a blue LED flashlight. As shown in FIG. 10, genomic DNA extracted using both protocols was successfully detected by observing green fluorescence from tube 2 and 3.

Example 9: Microsphere Separation and RT-LAMP to Detect Norovirus RNA

RNA extracted by microspheres and simple sample dilution, RT-LAMP amplification, and detection were compared. A Norovirus Group I (Recombinant) stool matrix was used as the sample for both dilution and microsphere extraction in tube. For the dilution protocol, the stool matrix was diluted to 1/10, 1/50, 1/100 and 1/500 of its original concentration using nuclease-free water, and 2 μL of each dilution was used as a sample for a RT-LAMP specific for the ORF1-ORF2 region of Norovirus group 1 gene. A negative control using 2 μl nuclease-free water was also included.

For RNA extraction using microspheres, 100 µL of stool matrix was mixed with microspheres and 1 ml 4 M guanidine thiocyanate lysis buffer in a 1.5 ml microcentrifuge tube, which was then inverted for 1 minute to release RNA and bind the released RNA to microspheres. A washing step of 1 ml 80% ethanol was further performed. After removing the ethanol, the microspheres were baked at 65° C. for 10 minutes using a heat block to let the residual ethanol evaporate, and then mixed with 50 µl nuclease-free water for RNA elution. A volume of 2 µl of elution buffer, 2 µl of a half dilution of the elution buffer and 2 µl of a 1/10 dilution of the elution buffer were used as samples for RT-LAMP. A negative control using 2 µl nuclease-free water was also included.

Each 25 µL of RT-LAMP system contains 2.5 µL of OX isothermal amplification buffer, 1.4 mM dNTPs, 6 mM MgSO$_4$, 2.5 µL of 10× primer mix, 8 U Bst 2.0 WarmStart® DNA Polymerase, 7.5 U WarmStart® RTx Reverse Transcriptase. All reagents in the RT-LAMP system were obtained from New England Biolabs (Ipswich, Mass., USA). The primer mix contains 1.6 µM of FIP and BIP primer and 0.2 µM of F3 and primer B3, obtained from Integrated DNA Technology (Skokie, Ill., USA). The sequences of these primers are listed in Table 6 The RT-LAMP was conducted by incubating the mixture at 65° C. degrees for 30 minutes using a heat block. The amplification was evaluated by mixing the amplicons with a SYBR Green I gel stain and observing the fluorescence of the SYBR-DNA complex under a blue LED flashlight.

TABLE 6

RT-LAMP primers sequences

| Oligo Name | Sequence |
| --- | --- |
| Norovirus G1 | |
| FIP | AGCGTCCTTAGACGCCATCATCACCTCGGATTGTGGACAGG (SEQ ID NO: 37) |
| BIP | GGCGCTGGTCAGTTGGTACCCGCTACAGGATCCATTGCA (SEQ ID NO: 38) |
| F3 | YATGTTCCGYTGGATGCG (SEQ ID NO: 39) |
| B3 | AACTTGCCCAGCAGTTGC (SEQ ID NO: 40) |
| Norovirus G2 | |
| Nov-G2-FIP | ATAGCGGCACCAACAACGGCCTCGTCCCAGAGGTCAAC (SEQ ID NO: 45) |
| Nov-G2-BIP | ACCTGTAGCGGGCCAACAACTCTCCACCAGGGGCTT (SEQ ID NO: 46) |
| Nov-G2-F3* | CCCATCTGATGGGTCCRCA (SEQ ID NO: 47) |
| Nov-G2-B3 | CACCTGGAGCGTTTCTAGG (SEQ ID NO: 48) |

*Note: Y is a mixture of C or T; R is a mixture of A or G

FIGS. 11A-11B indicate that the microspheres successfully extracted RNA from the stool matrix even after RNA elution and 1/10 dilution of the elution amplified by RT-LAMP. On the other hand, none of the direct dilutions of the stool matrix were amplified by RT-LAMP, indicating the stool matrix inhibited the reaction.

Example 10: Stool Purified Using Microspheres and Assayed on Lateral Flow Assay

LAMP master mix contains: 10× Bst DNA polymerase buffer II (NEB B0374S), 1 mM dNTPs (NEB N0446S), 200 nM Betaine (Sigma B0300), 7.5 pmol of F3 and B3 primer, 75 pmol of FIP and BIP primer, 30 pmol of LF and LB primer, and 8 U Bst DNA polymerase II (NEB M0537S). The sequences of C. diff LAMP primers are listed in Table 4. The LAMP master mix was made freshly before each test.

Microsphere sample preparation. 1-5 mg of stool sample was weighed into 1.5 ml microfuge tubes, then 1 ml 4M guanidinium thiocyanate solution was added and the mixture was vortexed. 100 µl stool lysis solution was added into 500 µl microfuge tubes pre-loaded with 3 mg microspheres. The microsphere tube was rotated end-over-end for 1 min, then the bottom liquid fraction was removed. The washing was performed by adding and then quickly removing 100 µl washing buffer (80% ethanol). To elute the separated DNA from the microspheres, 100 µl nuclease-free water was added. The DNA elution was ready to be used for downstream process or analysis.

LAMP Amplification. After microsphere separation, 2 µl of eluate was added into 23 µl LAMP master mix and incubated for 45 min at 65° C. After incubation, 10 µl of the LAMP amplicons and 100 µl running buffer were loaded onto the sample pad of the lateral flow strip. Visual identification was performed within 5-10 min.

Figure 12:
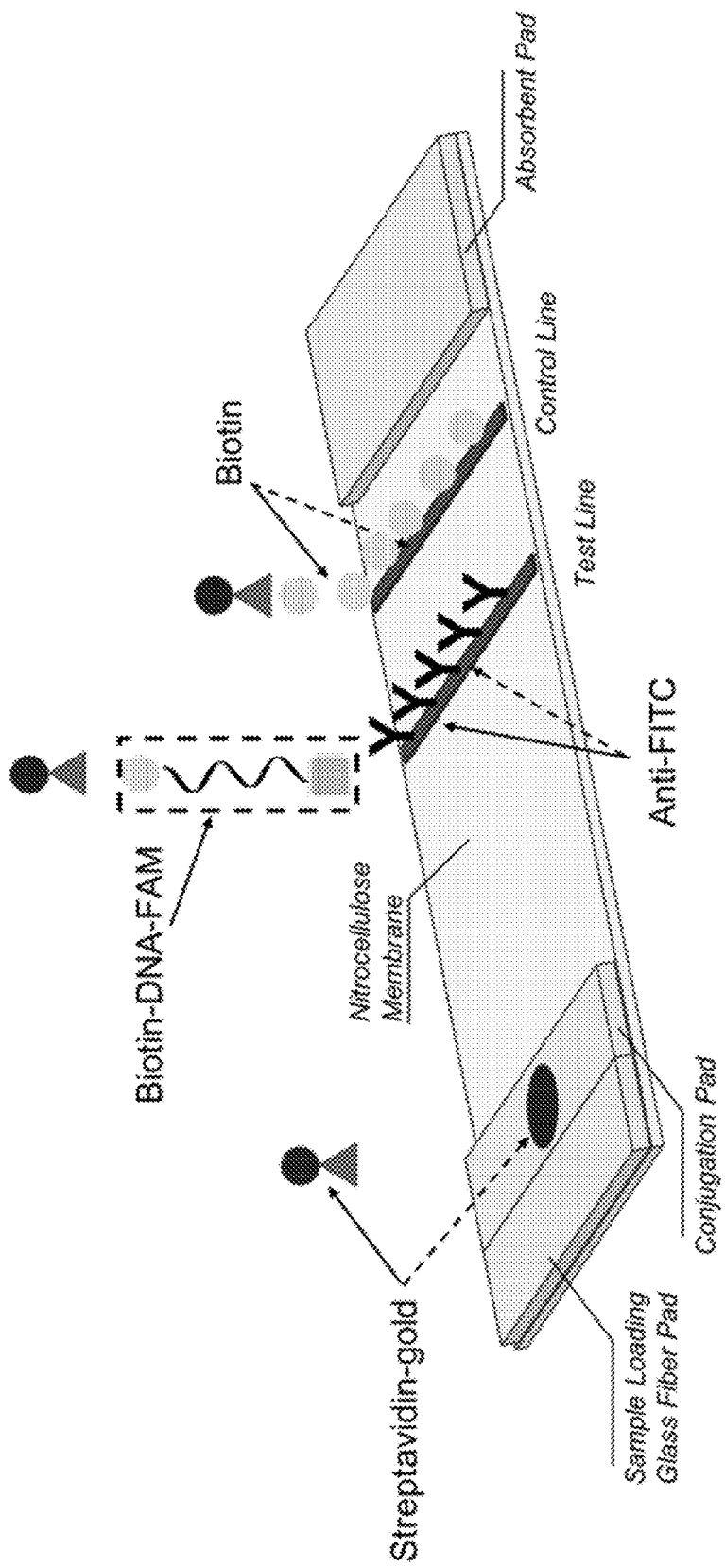
FIG. 12 schematically illustrates a lateral flow assay device.

Detection with lateral flow assay device. The lateral flow strip (Ustar, D003-03) has antiFITC and biotin printed at the test line and control line, respectively, as schematically illustrated in FIG. 12. The streptavidin gold nanoparticles were preloaded at the conjugation pad. Once the target sequences were successfully amplified by the LAMP assay, the amplicon would form a biotin-DNA-FAM structure, where the biotin functional group will bind to the streptavidin-gold and the FAM tag will be captured by the anti-FITC at the test line. If the LAMP assay did not work, the biotin-DNA-FAM sequence would not form, thus the test line would not show color. Regardless of the presence or absence of the amplicon, the streptavidin-gold will move to the top of the lateral flow assay and bind with the biotin at the control line area.

Figure 13:
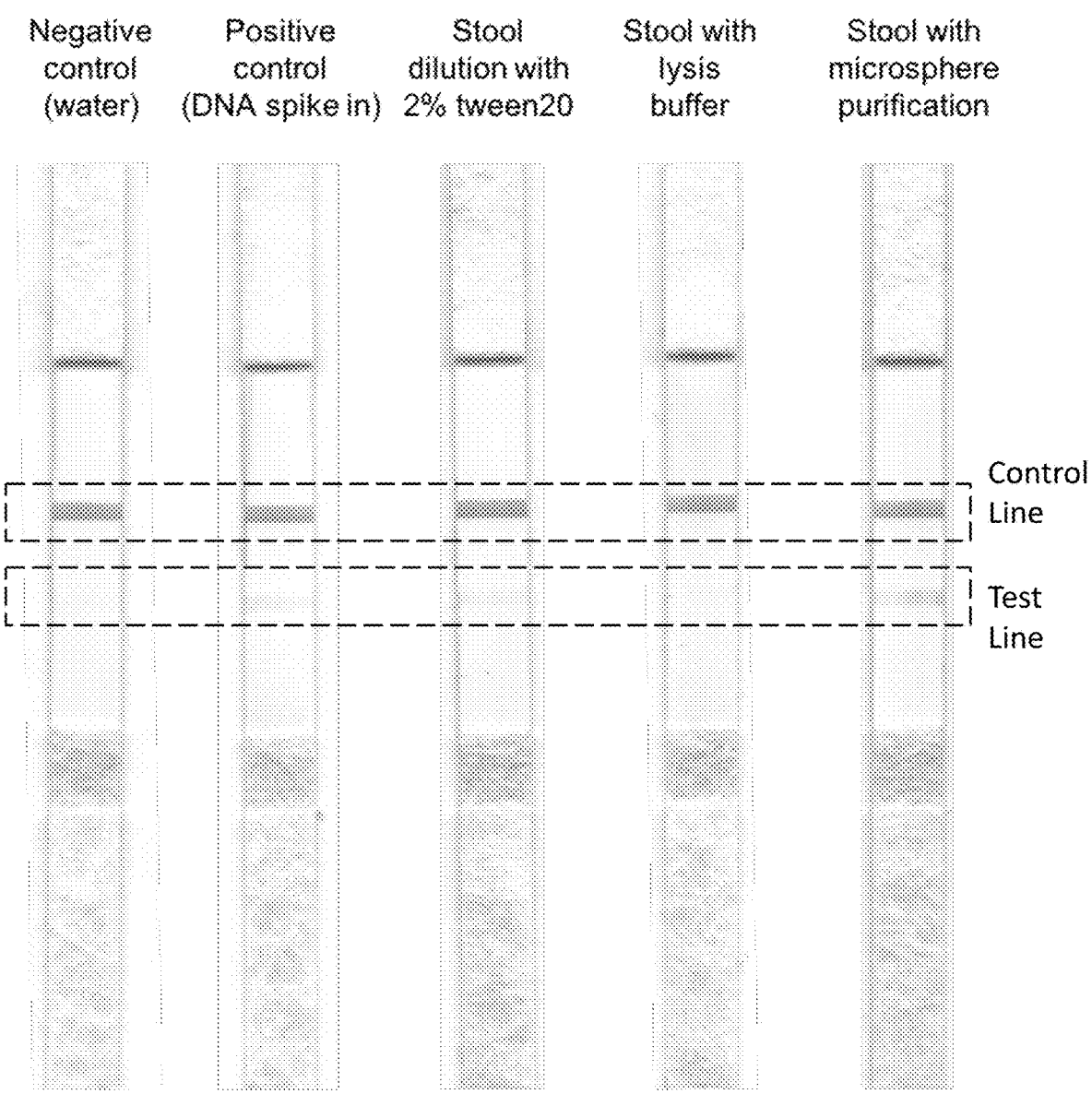
FIG. 13 shows lateral flow strips of: (a) Negative control, LAMP amplicon from water sample; (b) Positive control, LAMP amplicon from 1:100 dilution of commercially available *C. diff* genomic DNA; (c) LAMP amplicon from 5 mg *C. diff* positive human stool sample diluted in 1 ml 2% Tween 20 solution; (d) LAMP amplicon from 5 mg *C. diff* positive human stool sample diluted in 1 ml 4 M guanidium thiocyanate; and (e) LAMP amplicon from the eluates of microsphere separation process. Hashed boxes highlight the control and test lines.

As shown in FIG. 13, each of the positive control, stool with 2% tween20 dilution, and the stool with microsphere separation samples displayed a positive signal at the test line. This indicates that the microsphere method can capture target DNA and release the DNA for use with a lateral flow assay. The sample with microsphere separation displays a stronger signal intensity than the 2% tween20 dilution sample, which means the microsphere method concentrated the target DNA. In contrast to the positive signals obtained for the sample separated with the microspheres, the sample comprising stool with lysis buffer failed to display a positive test signal. This shows that lysing the stool sample, without further processing, is incapable of being amplified and detected with lateral flow device.

Example 11: Microsphere DNA Binding Kinetics

For the microsphere-DNA binding kinetic test, we performed a Qubit measurement of DNA (E. coli genomic DNA, ATCC, Manassas, Va.) diluted in water and 4M guanidinium thiocynate. The results showed that both samples have the same DNA concentration (±2 ng/ml). This result indicated that the Qubit test result is not affected by high concentration of salt.

Then, 5 mg microspheres were allowed to bind genomic DNA samples in 4 M guanidinium thiocyanate for 10 sec, 20 sec 30 sec, and 1 min, with and without end-to-end rotation by inversion, respectively. The DNA binding efficiency data was analyzed in Microsoft Excel. Here, the difference between initial DNA concentration and DNA concentration in the remaining liquid after microsphere binding was calculated at each desired time point, and then divided by the initial DNA concentration.

Figure 14:
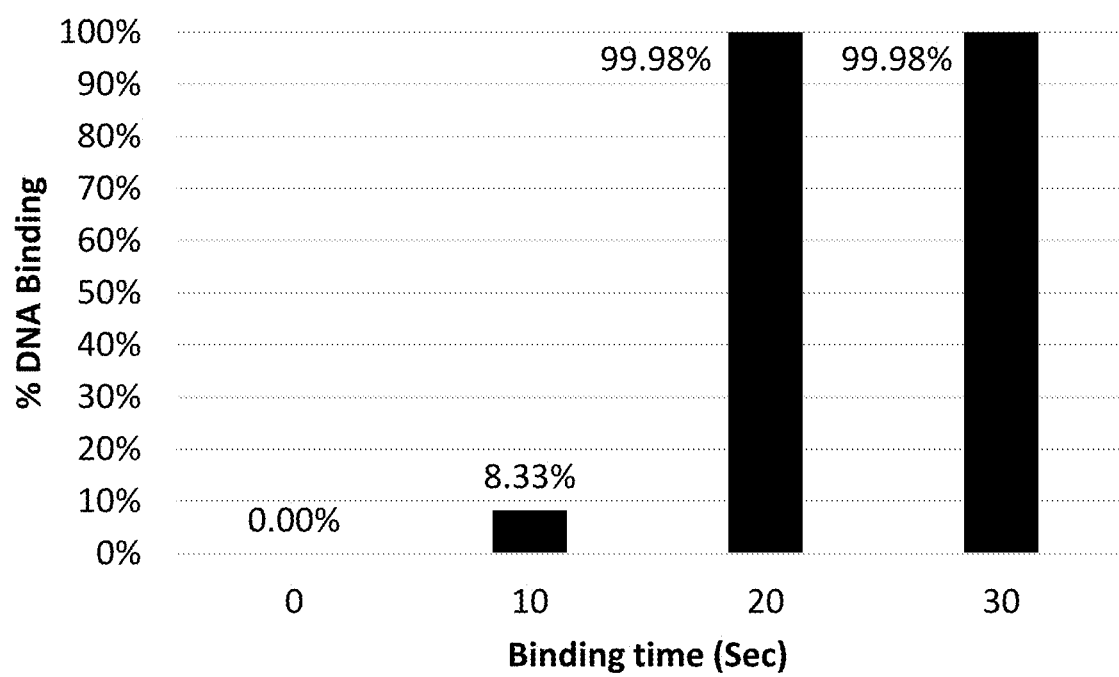
FIG. 14 demonstrates rapid DNA binding to microspheres with rotation.

When microspheres and DNA were mixed with end-to-end rotation by inversion, the initial DNA concentration was 60 ng/ml in a total volume of 100 µL. At 10 sec, the DNA concentration dropped to 55 ng/ml, then at 20 sec the DNA concentration in the remaining liquid was lower than detection range (<0.01 ng/ml). As shown in FIG. 14, the binding occurs at between 10 sec and 20 sec, and the binding efficiency is over 99.9%.

Figure 15:
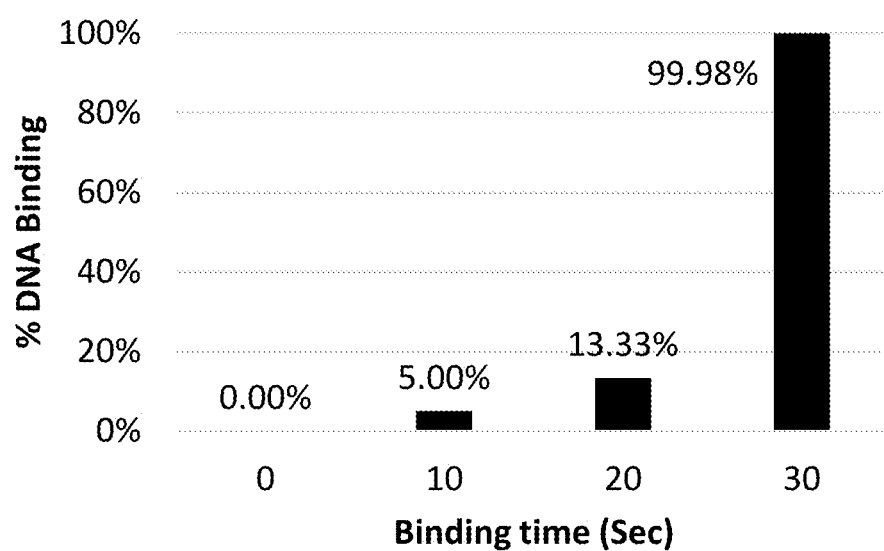
FIG. 15 demonstrates rapid DNA binding to microspheres without rotation.

When the microspheres and DNA were mixed without inversion and rotation, at 10 sec and 20 sec, the DNA concentration in the remaining buffer after capture were 57 and 52 ng/ml, respectively. But from 30 sec, the concentration dropped to lower than the detection range (<0.01 ng/ml), which means that even without inverting or rotating the tube, over 99.9% of DNA binding still occurs within 30 seconds (FIG. 15).

Example 12: Recovery of DNA from Microspheres

Figure 16:
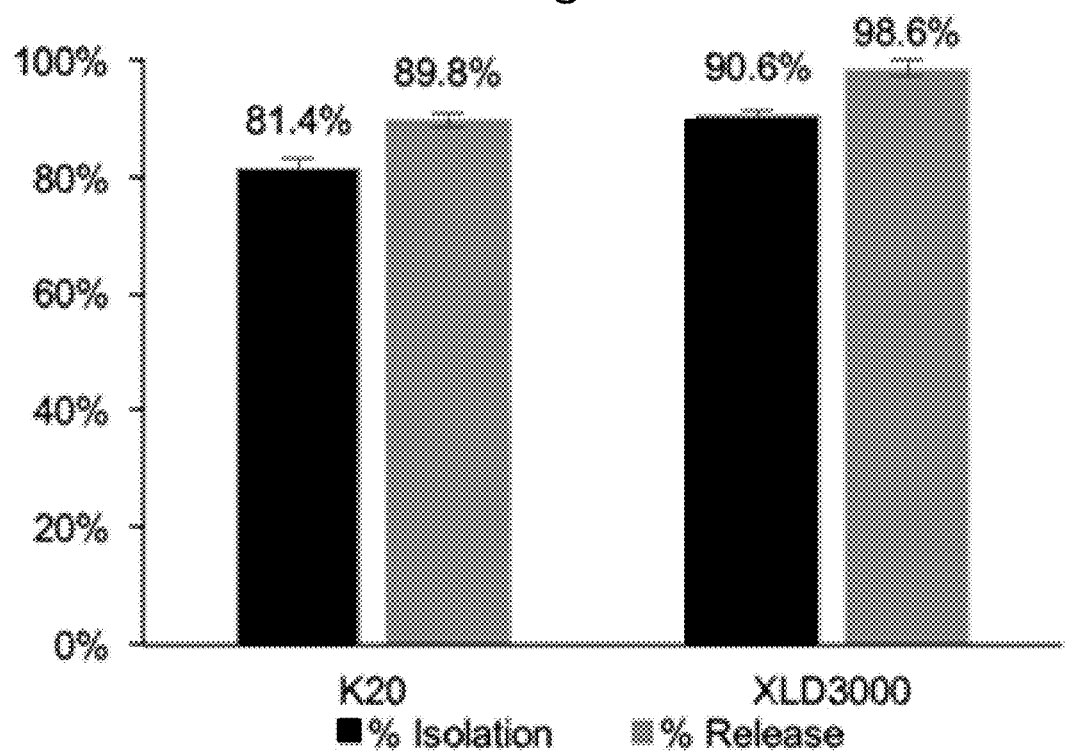
FIG. 16 demonstrates the effective isolation and release of nucleic acids from two different microspheres.

We used a Qubit fluorimeter to measure the % recovery of E. coli genomic DNA bound to and released from the microspheres. We used the Qubit to measure the initial concentration, remaining concentration after microsphere isolation, and the DNA concentration in the releasing buffer. The isolation and releasing efficiency of the two types microspheres are shown in FIG. 16. K20 and XLD3000 microspheres capture 81.4% and 90.6% of the nucleic acids, respectively. The are also capable of releasing 89.8% and 98.6% of the captured nucleic acids after washing, respectively. The high isolation and releasing efficiency indicated that the microsphere separation method worked with high yields for both capture and release.

Example 13: PCR Amplification of Nucleic Acids Separated by the Microspheres

Hollow-centered microspheres of 5 mg are loaded in a 1.5 ml microcentrifuge. A lysis buffer of 500 µL 4 M guanidine thiocyanate (Millipore Sigma, Burlington, Mass., USA) and 20 µL E. coli stool matrix was added to the tube which was placed on a rotator to rotate for 5 minutes to allow DNA binding. After the rotation, the tube was rested on a rack to allow the microspheres to float to the top. The lysis buffer was then carefully removed using a pipette. Three replicates of bound DNA were prepared to the effect of performing the following wash step one, two or three times. To wash the microspheres, 500 µL of 80% ethanol was added to the tube and briefly rotated, then the tube was rested on a rack to let the microspheres float to the top. The ethanol was carefully removed using a pipette, and the tube was placed on a heating block at 95° C. degrees for 5 minutes to evaporate the remaining ethanol. The DNA bound to the microspheres was eluted using 50 µL nuclease-free water. A 1 µL volume was removed from the eluate of and used as a sample for PCR to detect the extracted E. coli DNA. A 1 µL volume of unpurified stool matrix of was used directly for PCR as a comparison. A negative control using 1 µl of nuclease-free water was also included.

Each 50 µL PCR reaction contains 5 µL of 10× 10× DreamTaq Buffer®, 0.2 mM dNTPs, 1.25 U DreamTaq DNA polymerase and 1 µM forward (5'GCCATCTCCT-GATGACGC 3' (SEQ ID NO: 25)) and reverse primers (5' ATTTACCGCAGCCAGACG3' (SEQ ID NO: 26)). All reagents in the PCR system were obtained from ThermoFisher Scientific (Waltham, Mass., USA) except for the dNTPs from New England Biolabs (Ipswich, Mass., USA). The primers were obtained from Integrated DNA Technology (Skokie, Ill., USA). The PCR cycling was conducted following the manufacturer's protocol for 30 cycles using 53° C. degrees as the annealing temperature in a PTC-200 Thermocycler (MJ Research). The amplification result was evaluated by loading 1 µL amplicons to the AgilentDNA 1000 kit (Agilent Technologies, Wilmette, Ill., USA).

Figure 17:
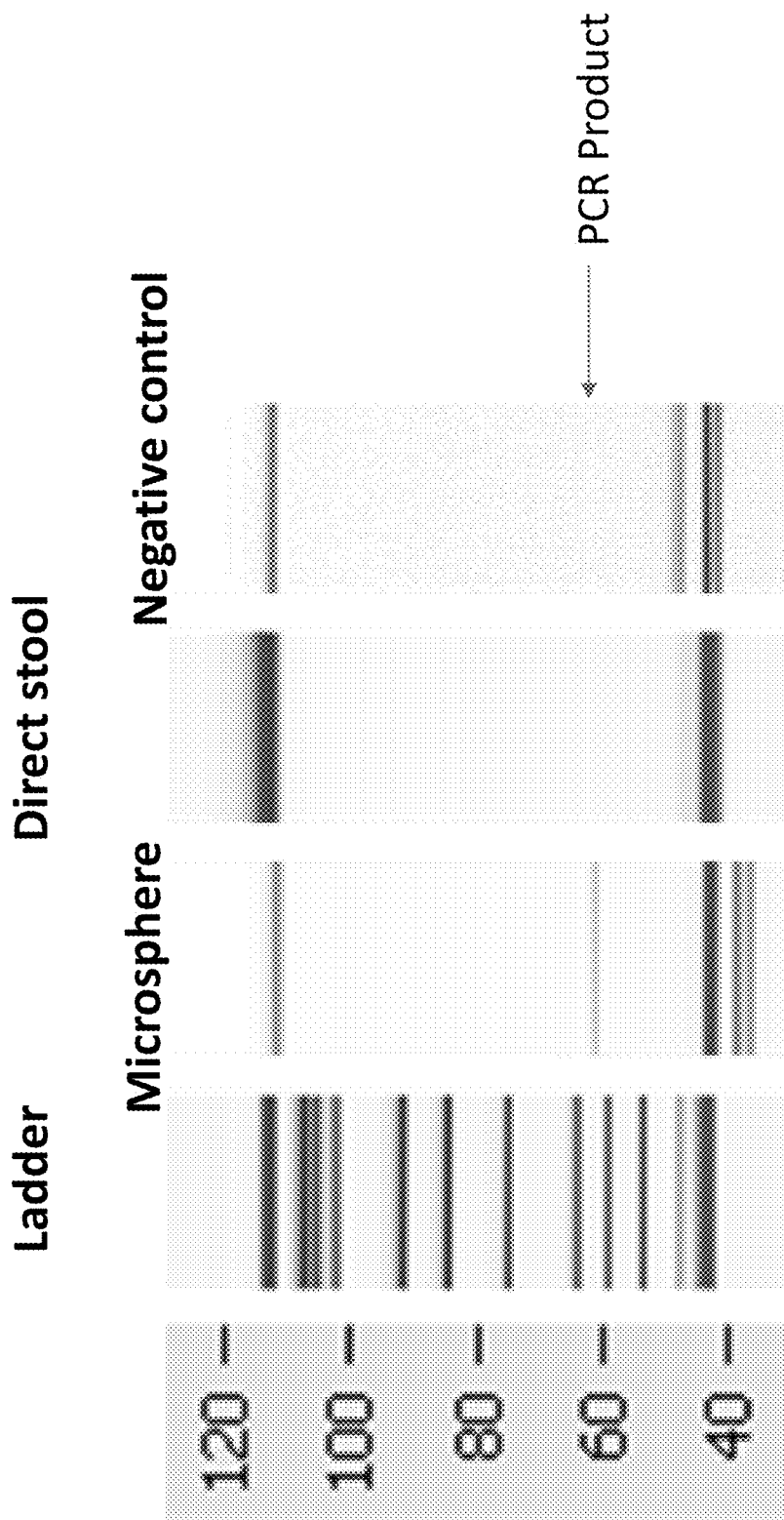
FIG. 17 demonstrates that DNA isolated with microspheres may be amplified by PCR.

The results are shown in FIG. 17. The PCR product was observed in the microsphere-purified sample (lane 2 marked "Microsphere" in FIG. 17) but not in the unpurified stool matrix or the negative control (no sample, pure water).

Example 14: Detection of E. coli Oligonucleotides in Stool Samples

Figure 18A:
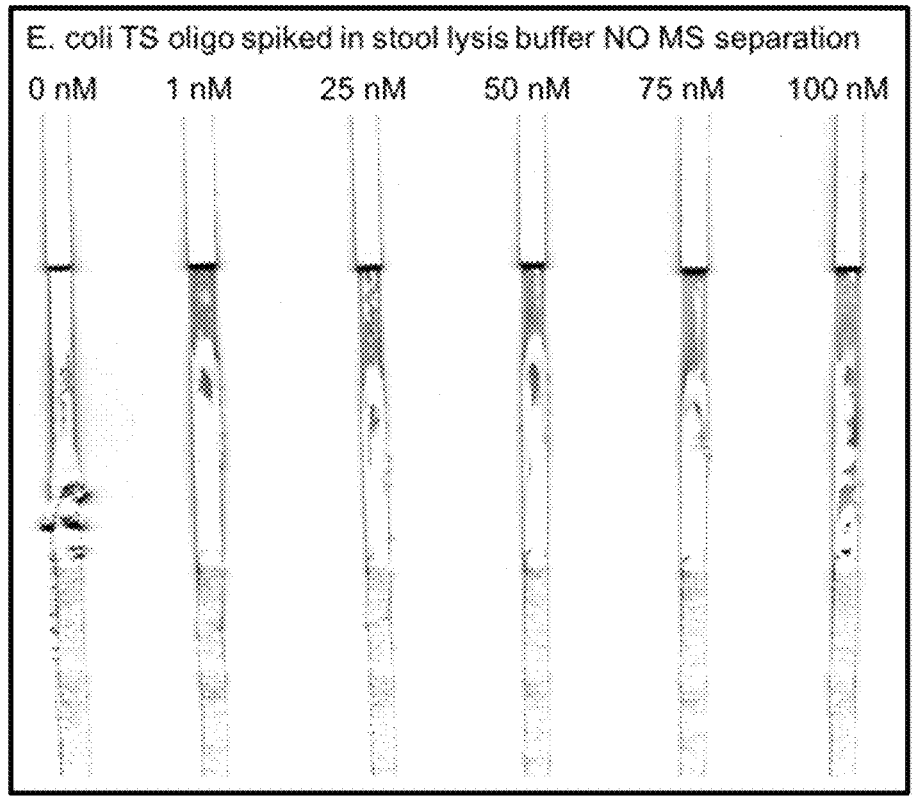
FIGS. 18A-18B show images of *E. coli* nitrocellulose diagnostic strips of (FIG. 18A) *E. coli* target sequences spiked in stool and lysis buffer without microsphere separation, and (FIG. 18B) *E. coli* target sequences spiked in stool and lysis buffer with microsphere separation.
Figure 18B:
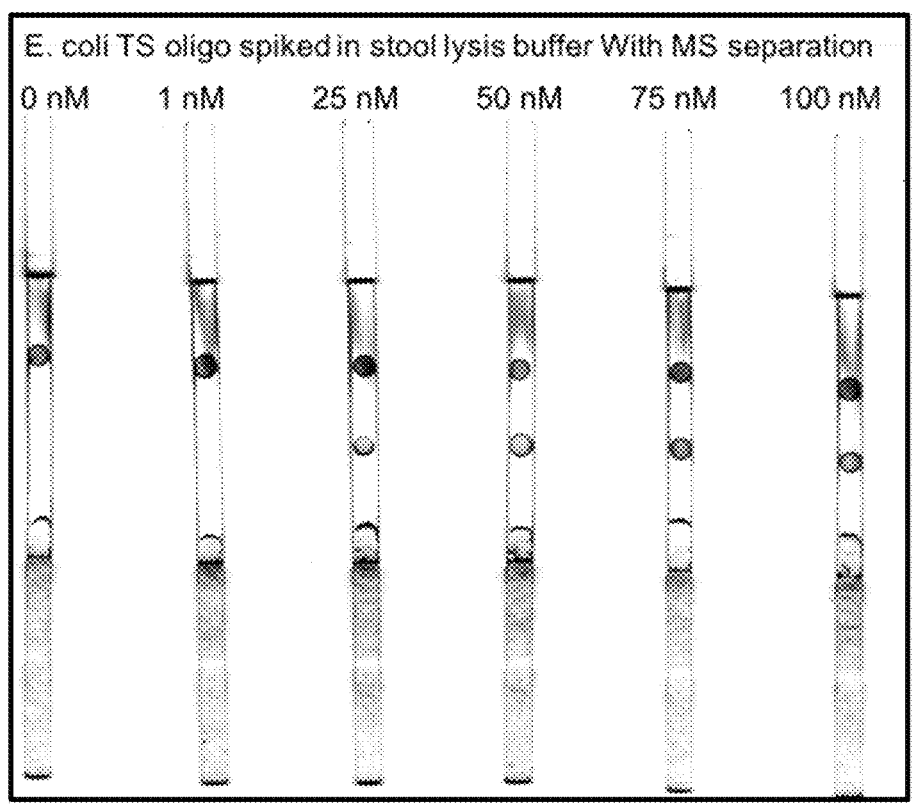

FIGS. 18A-18B depict the lateral flow results of the E. coli target sequence oligonucleotides spiked into healthy stool samples with and without the microsphere purification. The results indicate that the nitrocellulose membrane surfaces were totally eroded by the high concentration of chaotropic salt in the lysis buffer. However, the samples with microsphere separation not only eliminated the erosion problems, but also showed that oligonucleotides can be purified by microspheres and verified the integration of microsphere separation method and lateral flow molecular diagnostic device.

Figure 19:
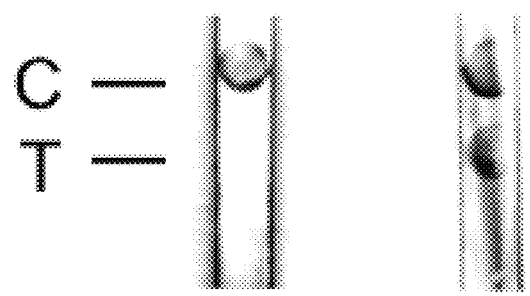
FIG. 19 shows lateral flow strip images of: (left) H20 microsphere separation of *Cryptosporidium* DNA and test on lateral flow assay; and (right) XLD 3000 microsphere separation of *Cryptosporidium* DNA and test on lateral flow assay. T: Test line. C: Control line.
Figure 20:
FIG. 20 shows fluorescent detection of microsphere-purified DNA from urine and saliva by LAMP. The tube in the left contains DNA purified from saliva (green), the tube in the middle contains DNA purified from urine (green), and the tube in the right is the negative control (dark).

Example 15: Comparison of Silica and Epoxy Silane Surfaced Microspheres 1,000 cryptosporidium oocysts were spiked in 4M guanidinium thiocyanate lysis buffer and separated by H20 (3M™ Glass Bubbles) microspheres having an epoxy silane surface treatment or XLD 3000 (3M™ Glass Bubbles) microspheres having a silica surface, respectively. The DNA eluents were then tested on Cryptosporidium lateral flow assay test strips. As shown in FIG. 19 (left), the H20 microspheres failed to separate the nucleic acids from the lysate. This is indicated by the lack of detected nucleic acids at the test line (T). In contrast, the XLD 3000 microspheres successfully separated and eluted the DNA, providing a positive signal at the test line (T).

Example 16: Microsphere Separated Nucleic Acids from Urine and Saliva Samples

Hollow-centered microspheres (5 mg) were loaded in a 1.5 ml microcentrifuge. Urine or saliva (100 µL volume) spiked with genomic DNA extracted from 10 µL Escherichia coli stool matrix was added to the tube and mixed with 500 µL lysis buffer (4 M guanidinium thiocyanate (Millipore Sigma, Burlington, Mass., USA). The genomic DNA was extracted using microspheres followed the same protocol described below. The tubes contained urine and saliva sample mixed with lysis buffer and microspheres were placed on a rotator to rotate for 5 minutes for DNA binding. After the rotation, the tube was rested on a rack to allow the microspheres float to the top. The lysis buffer was then carefully removed using a pipette. To wash the microspheres, 500 µL of 80% ethanol was added to the tube, briefly rotated and then the tube was rested on a rack to let the microspheres float to the top. The ethanol was carefully removed using a pipette, and the tube was further placed on a heating block at 95° C. degrees for 3 minutes to evaporate the remaining ethanol. The DNA bound to the microspheres was eluted using 50 µL nuclease-free water. An eluate of 2 µL was used as a sample was tested using a loop-mediated isothermal amplification (LAMP). Each 25 µL LAMP buffer contains 2.5 µL of 10× isothermal amplification buffer, 1.4 mM dNTPs, 6 mM MgSO$_4$, 2.5 µL of 10× primer mix, 8 U Bst 2.0 WarmStart® DNA Polymerase. All reagents in the LAMP system were obtained from New England Biolabs (Ipswich, Mass., USA). The primer mix contains 1.6 µM FIP (5'CATTTTGCAGCTGTACGCTCGCAGCCCATCAT-GAATGTTGCT3' (SEQ ID NO: 28))/BIP (5' CTGGGGCGAGGTCGTGGTATTCCGACAAACAC-CACGAATT3' (SEQ ID NO: 27)), 0.2 µM F3 (5' GCCATCTCCTGATGACGC 3' (SEQ ID NO: 25))/B3 (5' ATTTACCGCAGCCAGACG3' (SEQ ID NO: 26)), and 0.4 µM LF (5' CTTTGTAACAACCTGTCATCGACA3' (SEQ ID NO: 29))/LB (5'ATCAATCTCGATATCCAT-GAAGGTG3' (SEQ ID NO: 30)) was obtained from Integrated DNA Technology (Skokie, Ill., USA). The LAMP was conducted by incubating the mixture at 65° C. degrees for 30 minutes using a heat block. Nuclease-free water was used as sample for a negative control run.

The amplification result was evaluated by mixing the amplicons with a SYBR Green I gel stain and observing the fluorescence of the SYBR-DNA complex under a blue LED flashlight. The result is shown in FIG. 1, indicating microsphere-purified DNA from both urine and saliva samples were successfully detected by LAMP, with a green fluorescence observed from the left two tubes.

Example 17: Microsphere Separated Nucleic Acids from Urine and Blood Samples

10 µl 0.1 ng/ml C. diff genomic DNA and spiked in 100 µl PBS, human urine, and human blood sample respectively. 900 µl of 4M guanidinium thiocyanate solution was added to each sample and followed by vortex mixing. 100 µl of lysis solution from each sample was added into a 500 µl microfuge tube pre-loaded with 3 mg microspheres. Tubes were rotated end-to-end for 1 min followed by removal the bottom liquid fraction. Microspheres were washed by adding 100 µl washing buffer (80% ethanol) followed by removal of the washing buffer quickly. To elute the separated DNA from the surface of the microspheres, 100 µl nuclease free water was added. The DNA eluate was ready to be used for downstream process or analysis. After microsphere separation, 2 µl eluates were added into 23 µl LAMP master mix and incubated for 45 min at 65° C. After incubation, 2 µl LAMP amplicons were added into 10 µl 1:100 dilution of SYBR green to identify the fluorescent test results. At the same time, 10 µl of the LAMP amplicons and 100 µl running buffer were loaded onto the sample pad of the lateral flow strip. Visual identification can be done within 5-10 min.

Figure 21:
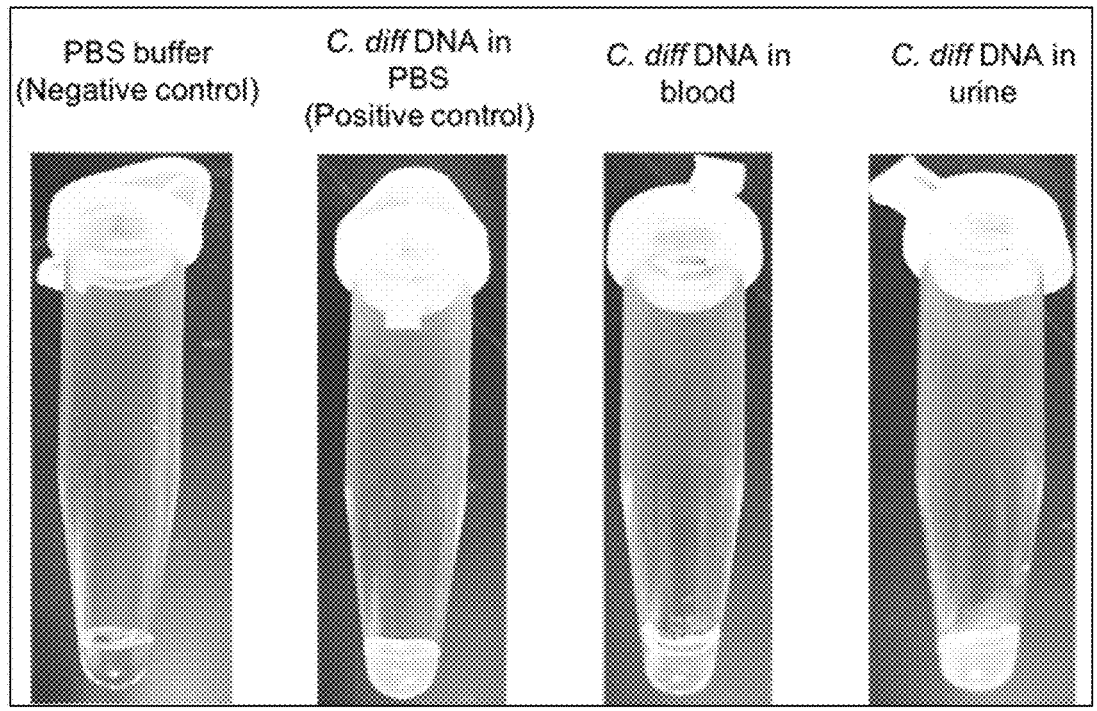
FIG. 21 show fluorescence LAMP DNA amplification after microsphere separation for: (a) PBS buffer (dark); (b) *C. diff* DNA spike in PBS buffer (green); (c) *C. diff* DNA spike in human blood sample (green); and (d) *C. diff* DNA spike in human urine sample (green).
Figure 22:
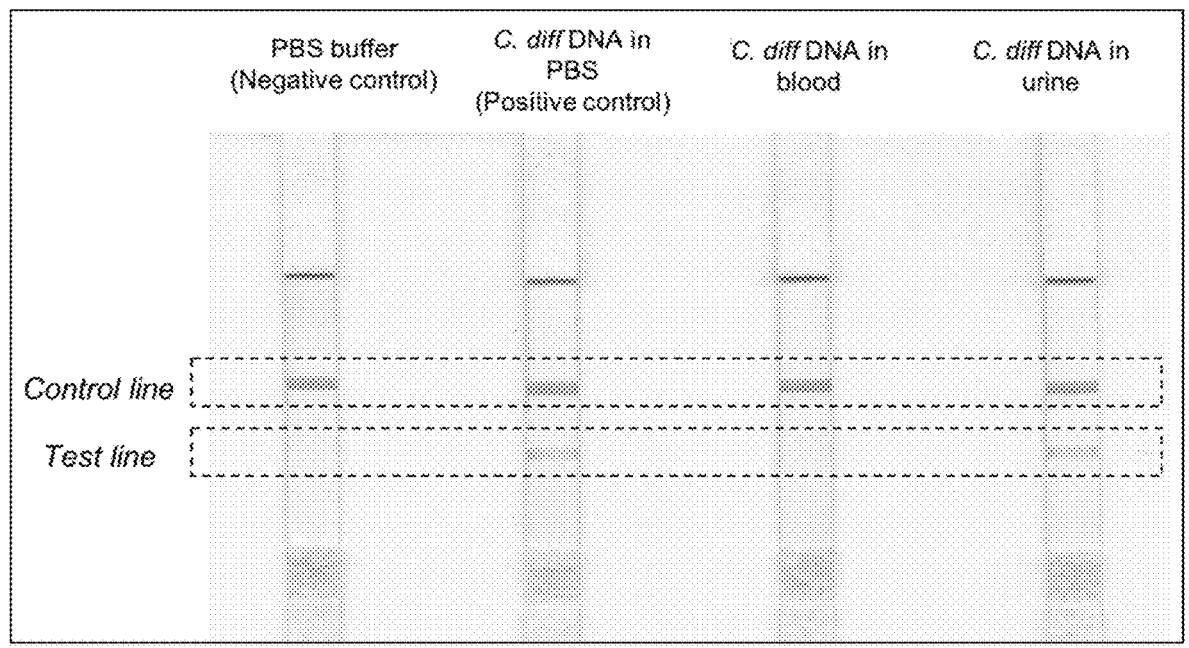
FIG. 22 lateral flow paper strip test results for LAMP DNA amplification after microsphere separation for: (a) PBS buffer (no positive test signal); (b) *C. diff* DNA spike in PBS buffer (positive test signal); (c) *C. diff* DNA spike in human blood sample (positive test signal); and (d) *C. diff* DNA spike in human urine sample (positive test signal).

FIG. 21 shows the fluorescent test after LAMP amplification from each sample types. Fluorescent signals were positively identified in the positive control, blood, and urine samples, demonstrating that the microsphere separation can effectively purify C. diff DNA out of those biological matrixes and amplify the target DNA via LAMP assay. The downstream lateral flow test also proved the microsphere separation and LAMP amplification. In FIG. 22, the positive test signals were identified in the positive control, blood, and urine samples. For comparison, the negative control sample failed to result in a positive test signal.

Example 18: Concentration of Samples Using Microspheres

To demonstrate sample concentration using microspheres, 10 µL and 100 µL Escherichia coli stool matrix (ZeptoMetrix Corporation, Buffalo, N.Y., USA) were used for DNA extraction using microspheres. Hollow-centered microspheres of 5 mg are loaded in a 1.5 ml microcentrifuge. Stool matrix of 10 or 100 µL were mixed with 500 µL lysis buffer (4 M guanidine thiocyanate (MilliporeSigma, Burlington, Mass., USA) and added to the microcentrifuge tubes with microspheres. The microcentrifuge tubes were then placed on a rotator to rotate for 5 minutes for DNA binding. After the rotation, the tube was rested on a rack to allow the microspheres float to the top. The lysis buffer was then carefully removed using a pipette. To wash the microspheres, 500 µL of 80% ethanol was added to the tube, briefly rotated and then the tube was rested on a rack to let the microspheres float to the top. The ethanol was carefully removed using a pipette, and the tube was further placed on a heating block at 95° C. degrees for 5 minutes to evaporate the remaining ethanol. The DNA bond to the microspheres was eluted using 100 µL nuclease-free water. The elute from both 10 and 100 µL stool matrix, and 10- and 100-times dilution of the elutes were amplified using LAMP. The sample volume of 2 µL was used. Each 25 µL LAMP buffer contains 2.5 µL of 10× isothermal amplification buffer, 1.4 mM dNTPs, 6 mM MgSO$_4$, 2.5 µL of 10× primer mix, 8 U Bst 2.0 WarmStart® DNA Polymerase. All reagents in the LAMP system was obtained from New England Biolabs (Ipswich, Mass., USA). The primer mix (E. coli primer mix in Table 4) contains 1.6 µM FIP/BIP, 0.2 µM F3/B3, and 0.4 µM LF/LB was obtained from Integrated DNA Technology (Skokie, Ill., USA). The LAMP was conducted by incubating the mixture at 65° C. degrees for 30 minutes using a heat block. Nuclease-free water was used as sample for a negative control run.

Figure 23:
FIG. 23 shows the detection of DNA extracted from 10 and 100 µL stool matrix using microspheres. Tube 1-3 are the elution buffer and 10- and 100-times dilution of 10 µL microspheres. Tube 5-7 are the elution buffer and 10- and 100-times dilution of 100 µL microspheres. Tube 4 and 8 are negative controls.
Figure 23:
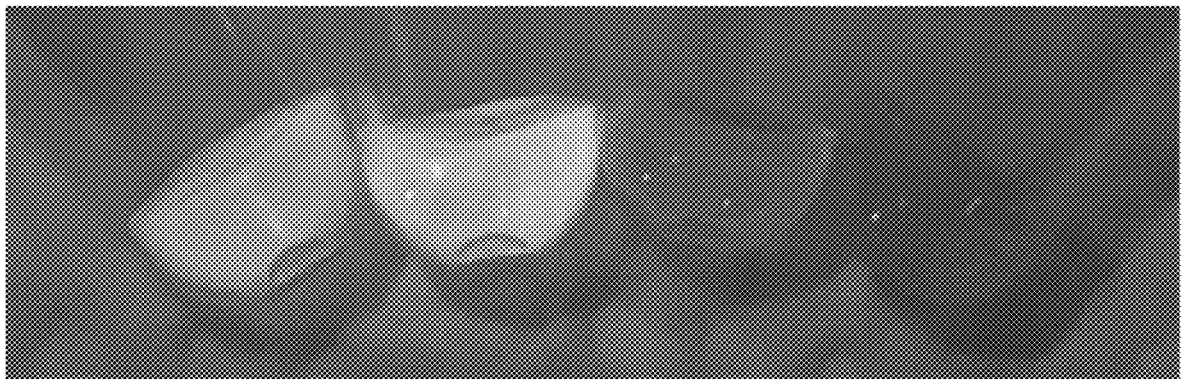

The amplification result was evaluated by mixing the amplicons with a SYBR Green I gel stain and observing the fluorescence of the SYBR-DNA complex under a blue LED flashlight. The result is shown in FIG. 23, tube 1~3 are elution and dilutions of 10 µL stool matrix while tube 5~7 are elution and dilutions of 100 µL stool matrix. Tube 4 and 8 are negative controls. The amplification results indicate, by using 10 times more stool matrix, both the undiluted elution buffer and the 10-times dilution of the elution buffer could be detected by LAMP, while when using less stool matrix, only the undiluted elution buffer could be detected.

We claim:

1. A method for separating a nucleic acid from a sample, the method comprising:
   (a) contacting a sample lysate with a plurality of nucleic-acid-capture microspheres within a microsphere-separating device comprising a microsphere retaining mesh, to form a lysate dispersion; wherein the lysate dispersion comprises a lysate continuous phase and a particulate phase and wherein the particulate phase comprises the plurality of nucleic-acid-capture microspheres and an adsorbed nucleic acid obtained from the sample;
   (b) mechanically separating the lysate continuous phase from the particulate phase comprising the plurality of nucleic-acid-capture microspheres and the adsorbed nucleic acid obtained from the sample; and
   (c) contacting the particulate phase with an eluent to form an eluate comprising the nucleic acid obtained from the sample
   wherein the plurality of nucleic-acid-capture microspheres comprise soda-lime-borosilicate microspheres.

2. A method for amplifying a nucleic acid separated from a sample, the method comprising:
   separating the nucleic acid from the sample; wherein separating the nucleic acid from the sample comprises:
   (a) contacting a sample lysate with a plurality of nucleic-acid-capture microspheres within a microsphere-separating device comprising a microsphere retaining mesh to form a lysate dispersion; wherein the lysate dispersion comprises a lysate continuous phase and a particulate phase and wherein the particulate phase comprises the plurality of nucleic-acid-capture microspheres and an adsorbed nucleic acid obtained from the sample;
   (b) mechanically separating the lysate continuous phase from the particulate phase comprising the plurality of nucleic-acid-capture microspheres and the adsorbed nucleic acid obtained from the sample; and
   (c) contacting the particulate phase with an eluent to form an eluate comprising the nucleic acid obtained from the sample;
   contacting the nucleic acid separated from the sample with an amplification medium; and
   amplifying the nucleic acid separated from the sample,
   wherein the plurality of nucleic-acid-capture microspheres comprises soda-lime-borosilicate microspheres.

3. The method of claim 2, wherein the nucleic acid separated from the sample is amplified by a polymerase chain reaction (PCR) technique or an isothermal amplification technique.

4. The method of claim 2, wherein the amplification medium comprises a primer complementary to a target sequence indicative of a pathogen or a cell present in the sample.

5. A method of detecting a nucleic acid in a sample indicative of a pathogen or a cell, the method comprising:
   separating the nucleic acid from the sample, wherein separating the nucleic acid from the sample comprises:
   (a) contacting a sample lysate with a plurality of nucleic-acid-capture microspheres within a microsphere-separating device comprising a microsphere retaining mesh to form a lysate dispersion; wherein the lysate dispersion comprises a lysate continuous phase and a particulate phase and wherein the particulate phase comprises the plurality of nucleic-acid-capture microspheres and an adsorbed nucleic acid obtained from the sample;
   (b) mechanically separating the lysate continuous phase from the particulate phase comprising the plurality of nucleic-acid-capture microspheres and the adsorbed nucleic acid obtained from the sample; and
   (c) contacting the particulate phase with an eluent to form an eluate comprising the nucleic acid obtained from the sample;

contacting the nucleic acid separated from the sample with an amplification medium, wherein the amplification medium comprises a primer complementary to a target sequence indicative of the pathogen or the cell;

amplifying the nucleic acid separated from the sample to form an amplified sample comprising a plurality of amplicons of the target sequence; and detecting the target sequence indicative of the pathogen or the cell, wherein the plurality of nucleic-acid-capture microspheres comprises soda-lime-borosilicate microspheres.

6. The method of claim 5, wherein the detecting step comprises:

loading a lateral flow device with the amplified sample; and detecting a trimolecular hydridization or binding of (1) the target sequence, (2) a detectably labelled probe, and (3) a capture probe;

wherein the lateral flow device comprises:

a loading area positioned at one end of the lateral flow device, an area comprising the detectably labelled probe, wherein said detectably labelled probe is not bound to the lateral flow device and is capable of wicking across at least a portion of the lateral flow device; and an area comprising the capture probe, wherein said capture probe is immobilized on the lateral flow device.

7. The method of claim 5, wherein the nucleic acid obtained from the sample is amplified by an isothermal amplification technique.

8. The method of claim 5, wherein the plurality of nucleic-acid-capture microspheres comprise unicellular hollow microspheres having a diameter between 5 and 300 μm and a true particle density between 0.05 and 0.60 grams/cm$^3$.

9. The method of claim 5, wherein the method further comprises contacting the sample with a lysis or denaturing agent to prepare the sample lysate and washing the particulate phase with a washing medium prior to contacting the particulate phase with the eluent to form the eluate.

* * * * *

SEQUENCE LISTING

```
<160> NUMBER OF SEQ ID NOS: 48

<210> SEQ ID NO 1
<211> LENGTH: 29
<212> TYPE: DNA
<213> ORGANISM: Artificial
<220> FEATURE:
<223> OTHER INFORMATION: E-DC probe
```

```
<400> SEQUENCE: 1
gagcgttctg taagcctgcg aaaaaaaaa                                          29

<210> SEQ ID NO 2
<211> LENGTH: 29
<212> TYPE: DNA
<213> ORGANISM: Artificial
<220> FEATURE:
<223> OTHER INFORMATION: E-C probe

<400> SEQUENCE: 2
aaaaaaaata cctccagcat gcctcacag                                          29

<210> SEQ ID NO 3
<211> LENGTH: 29
<212> TYPE: DNA
<213> ORGANISM: Artificial
<220> FEATURE:
<223> OTHER INFORMATION: E-D probe

<400> SEQUENCE: 3
tcgcaggctt acagaacgct caaaaaaaa                                          29

<210> SEQ ID NO 4
<211> LENGTH: 29
<212> TYPE: DNA
<213> ORGANISM: Artificial
<220> FEATURE:
<223> OTHER INFORMATION: CD-DC probe

<400> SEQUENCE: 4
ccacatgtcc ttacggtcat gaaaaaaaa                                          29

<210> SEQ ID NO 5
<211> LENGTH: 29
<212> TYPE: DNA
<213> ORGANISM: Artificial
<220> FEATURE:
<223> OTHER INFORMATION: CD-C probe

<400> SEQUENCE: 5
aaaaaaaagt agggagcttc cccatacgg                                          29

<210> SEQ ID NO 6
<211> LENGTH: 29
<212> TYPE: DNA
<213> ORGANISM: Artificial
<220> FEATURE:
<223> OTHER INFORMATION: CD-D probe

<400> SEQUENCE: 6
catgaccgta aggacatgtg gaaaaaaaa                                          29

<210> SEQ ID NO 7
<211> LENGTH: 32
<212> TYPE: DNA
<213> ORGANISM: Artificial
<220> FEATURE:
<223> OTHER INFORMATION: CRF-DC probe

<400> SEQUENCE: 7
agcctgagaa acggctacca catcaaaaaa aa                                      32
```

```
<210> SEQ ID NO 8
<211> LENGTH: 29
<212> TYPE: DNA
<213> ORGANISM: Artificial
<220> FEATURE:
<223> OTHER INFORMATION: CRF-C probe

<400> SEQUENCE: 8
aaaaaaaagt aatttgcgcg cctgctgcc                                       29

<210> SEQ ID NO 9
<211> LENGTH: 32
<212> TYPE: DNA
<213> ORGANISM: Artificial
<220> FEATURE:
<223> OTHER INFORMATION: CRF-D probe

<400> SEQUENCE: 9
gatgtggtag ccgtttctca ggctaaaaaa aa                                   32

<210> SEQ ID NO 10
<211> LENGTH: 29
<212> TYPE: DNA
<213> ORGANISM: Artificial
<220> FEATURE:
<223> OTHER INFORMATION: GRD-DC probe

<400> SEQUENCE: 10
gtcaagctca gcaacatgaa caaaaaaaa                                       29

<210> SEQ ID NO 11
<211> LENGTH: 29
<212> TYPE: DNA
<213> ORGANISM: Artificial
<220> FEATURE:
<223> OTHER INFORMATION: GRD-C probe

<400> SEQUENCE: 11
aaaaaaaatc ttgtcgtgga acctgctga                                       29

<210> SEQ ID NO 12
<211> LENGTH: 29
<212> TYPE: DNA
<213> ORGANISM: Artificial
<220> FEATURE:
<223> OTHER INFORMATION: GRD-D probe

<400> SEQUENCE: 12
gttcatgttg ctgagcttga caaaaaaaa                                       29

<210> SEQ ID NO 13
<211> LENGTH: 29
<212> TYPE: DNA
<213> ORGANISM: Artificial
<220> FEATURE:
<223> OTHER INFORMATION: Camp-DC probe

<400> SEQUENCE: 13
cacaagttga gtagggaaag taaaaaaaa                                       29

<210> SEQ ID NO 14
<211> LENGTH: 29
<212> TYPE: DNA
<213> ORGANISM: Artificial
<220> FEATURE:
<223> OTHER INFORMATION: Camp-C probe
```

```
<400> SEQUENCE: 14
aaaaaaaaac tatatagtct catcctaca                                29

<210> SEQ ID NO 15
<211> LENGTH: 29
<212> TYPE: DNA
<213> ORGANISM: Artificial
<220> FEATURE:
<223> OTHER INFORMATION: Camp-D probe

<400> SEQUENCE: 15
actttcccta ctcaacttgt gaaaaaaaa                                29

<210> SEQ ID NO 16
<211> LENGTH: 29
<212> TYPE: DNA
<213> ORGANISM: Artificial
<220> FEATURE:
<223> OTHER INFORMATION: Noro-DC probe

<400> SEQUENCE: 16
atgatgcaga ctactctcgt taaaaaaaa                                29

<210> SEQ ID NO 17
<211> LENGTH: 29
<212> TYPE: DNA
<213> ORGANISM: Artificial
<220> FEATURE:
<223> OTHER INFORMATION: Noro-C probe

<400> SEQUENCE: 17 aaaaaaaag tactgccctc tgttgtgtt                                 29

<210> SEQ ID NO 18
<211> LENGTH: 29
<212> TYPE: DNA
<213> ORGANISM: Artificial
<220> FEATURE:
<223> OTHER INFORMATION: Noro-D probe

<400> SEQUENCE: 18
aacgagagta gtctgcatca taaaaaaaa                                29

<210> SEQ ID NO 19
<211> LENGTH: 29
<212> TYPE: DNA
<213> ORGANISM: Artificial
<220> FEATURE:
<223> OTHER INFORMATION: ETEC TOX-DC probe

<400> SEQUENCE: 19
atctttcccc tcttttagtc aaaaaaaaa                                29

<210> SEQ ID NO 20
<211> LENGTH: 29
<212> TYPE: DNA
<213> ORGANISM: Artificial
<220> FEATURE:
<223> OTHER INFORMATION: ETEC TOX-C probe

<400> SEQUENCE: 20
aaaaaaaatt ttgaagagtc aagtgattc                                29
```

```
<210> SEQ ID NO 21
<211> LENGTH: 29
<212> TYPE: DNA
<213> ORGANISM: Artificial
<220> FEATURE:
<223> OTHER INFORMATION: ETEC TOX-D probe

<400> SEQUENCE: 21
tgactaaaag aggggaaaga taaaaaaaa                              29

<210> SEQ ID NO 22
<211> LENGTH: 29
<212> TYPE: DNA
<213> ORGANISM: Artificial
<220> FEATURE:
<223> OTHER INFORMATION: EPEC-DC probe

<400> SEQUENCE: 22
cagcccggag ggctgcatta caaaaaaaa                              29

<210> SEQ ID NO 23
<211> LENGTH: 29
<212> TYPE: DNA
<213> ORGANISM: Artificial
<220> FEATURE:
<223> OTHER INFORMATION: EPEC-C probe

<400> SEQUENCE: 23
aaaaaaaagc tcggctttca gccctcttg                              29

<210> SEQ ID NO 24
<211> LENGTH: 29
<212> TYPE: DNA
<213> ORGANISM: Artificial
<220> FEATURE:
<223> OTHER INFORMATION: EPEC-D probe

<400> SEQUENCE: 24
gtaatgcagc cctccgggct gaaaaaaaa                              29

<210> SEQ ID NO 25
<211> LENGTH: 18
<212> TYPE: DNA
<213> ORGANISM: Artificial
<220> FEATURE:
<223> OTHER INFORMATION: E-F3 primer

<400> SEQUENCE: 25
gccatctcct gatgacgc                                          18

<210> SEQ ID NO 26
<211> LENGTH: 18
<212> TYPE: DNA
<213> ORGANISM: Artificial
<220> FEATURE:
<223> OTHER INFORMATION: E-B3 primer

<400> SEQUENCE: 26
atttaccgca gccagacg                                          18

<210> SEQ ID NO 27
<211> LENGTH: 40
<212> TYPE: DNA
<213> ORGANISM: Artificial
<220> FEATURE:
<223> OTHER INFORMATION: E-BIP primer
```

```
<400> SEQUENCE: 27
ctggggcgag gtcgtggtat tccgacaaac accacgaatt                           40

<210> SEQ ID NO 28
<211> LENGTH: 42
<212> TYPE: DNA
<213> ORGANISM: Artificial
<220> FEATURE:
<223> OTHER INFORMATION: E-FIP primer

<400> SEQUENCE: 28
cattttgcag ctgtacgctc gcagcccatc atgaatgttg ct                       42

<210> SEQ ID NO 29
<211> LENGTH: 24
<212> TYPE: DNA
<213> ORGANISM: Artificial
<220> FEATURE:
<223> OTHER INFORMATION: E-LF primer

<400> SEQUENCE: 29
ctttgtaaca acctgtcatc gaca                                            24

<210> SEQ ID NO 30
<211> LENGTH: 25
<212> TYPE: DNA
<213> ORGANISM: Artificial
<220> FEATURE:
<223> OTHER INFORMATION: E-LB primer

<400> SEQUENCE: 30
atcaatctcg atatccatga aggtg                                           25

<210> SEQ ID NO 31
<211> LENGTH: 23
<212> TYPE: DNA
<213> ORGANISM: Artificial
<220> FEATURE:
<223> OTHER INFORMATION: CD-F3 primer

<400> SEQUENCE: 31
gtatcaactg cattagatga aac                                             23

<210> SEQ ID NO 32
<211> LENGTH: 22
<212> TYPE: DNA
<213> ORGANISM: Artificial
<220> FEATURE:
<223> OTHER INFORMATION: CD-B3 primer

<400> SEQUENCE: 32
ccaaagatga agtaatgatt gc                                              22

<210> SEQ ID NO 33
<211> LENGTH: 48
<212> TYPE: DNA
<213> ORGANISM: Artificial
<220> FEATURE:
<223> OTHER INFORMATION: CD-FIB primer

<400> SEQUENCE: 33
ctgcacctaa acttacacca tctatcttcc tacattatct gaaggatt                  48
```

```
<210> SEQ ID NO 34
<211> LENGTH: 44
<212> TYPE: DNA
<213> ORGANISM: Artificial
<220> FEATURE:
<223> OTHER INFORMATION: CD-BIP primer

<400> SEQUENCE: 34
gagctaagtg aaacgagtga cccgctgttg ttaaatttac tgcc            44

<210> SEQ ID NO 35
<211> LENGTH: 18
<212> TYPE: DNA
<213> ORGANISM: Artificial
<220> FEATURE:
<223> OTHER INFORMATION: CD-FL-FAM primer

<400> SEQUENCE: 35
aatagttgca attatagg                                          18

<210> SEQ ID NO 36
<211> LENGTH: 26
<212> TYPE: DNA
<213> ORGANISM: Artificial
<220> FEATURE:
<223> OTHER INFORMATION: CD-BL-BIO primer

<400> SEQUENCE: 36
agacaagaaa tagaagctaa gatagg                                 26

<210> SEQ ID NO 37
<211> LENGTH: 41
<212> TYPE: DNA
<213> ORGANISM: Artificial
<220> FEATURE:
<223> OTHER INFORMATION: FIP primer

<400> SEQUENCE: 37
agcgtcctta gacgccatca tcacctcgga ttgtggacag g                41

<210> SEQ ID NO 38
<211> LENGTH: 39
<212> TYPE: DNA
<213> ORGANISM: Artificial
<220> FEATURE:
<223> OTHER INFORMATION: BIP primer

<400> SEQUENCE: 38
ggcgctggtc agttggtacc cgctacagga tccattgca                   39

<210> SEQ ID NO 39
<211> LENGTH: 18
<212> TYPE: DNA
<213> ORGANISM: Artificial
<220> FEATURE:
<223> OTHER INFORMATION: F3 primer
<220> FEATURE:
<221> NAME/KEY: misc_feature
<222> LOCATION: (1)..(1)
<223> OTHER INFORMATION: N is a C or T
<220> FEATURE:
<221> NAME/KEY: misc_feature
<222> LOCATION: (10)..(10)
<223> OTHER INFORMATION: N is a C or T

<400> SEQUENCE: 39
natgttccgn tggatgcg                                          18
```

```
<210> SEQ ID NO 40
<211> LENGTH: 18
<212> TYPE: DNA
<213> ORGANISM: Artificial
<220> FEATURE:
<223> OTHER INFORMATION: B3 primer

<400> SEQUENCE: 40
aacttgccca gcagttgc                                              18

<210> SEQ ID NO 41
<211> LENGTH: 19
<212> TYPE: DNA
<213> ORGANISM: Artificial
<220> FEATURE:
<223> OTHER INFORMATION: EPEC-F3 primer

<400> SEQUENCE: 41
cgacgatttg gtcgttgaa                                             19

<210> SEQ ID NO 42
<211> LENGTH: 18
<212> TYPE: DNA
<213> ORGANISM: Artificial
<220> FEATURE:
<223> OTHER INFORMATION: EPEC-B3 primer

<400> SEQUENCE: 42
tgtcatcggt catgttgc                                              18

<210> SEQ ID NO 43
<211> LENGTH: 51
<212> TYPE: DNA
<213> ORGANISM: Artificial
<220> FEATURE:
<223> OTHER INFORMATION: EPEC-FIP-FAM primer

<400> SEQUENCE: 43
caaaatgatc tgctgaccag gcttttttaag catttataca gttctgaaag c        51

<210> SEQ ID NO 44
<211> LENGTH: 52
<212> TYPE: DNA
<213> ORGANISM: Artificial
<220> FEATURE:
<223> OTHER INFORMATION: EPEC-BIP-BIO primer

<400> SEQUENCE: 44
acagtgcact accacttta ggttttcat tttagtcagt ttattcgtgt ga          52

<210> SEQ ID NO 45
<211> LENGTH: 38
<212> TYPE: DNA
<213> ORGANISM: Artificial
<220> FEATURE:
<223> OTHER INFORMATION: Nov-G2-FIP primer

<400> SEQUENCE: 45
atagcggcac caacaacggc ctcgtcccag aggtcaac                        38

<210> SEQ ID NO 46
<211> LENGTH: 36
<212> TYPE: DNA
<213> ORGANISM: Artificial
<220> FEATURE:
<223> OTHER INFORMATION: Nov-G2-BIP primer
```

```
<400> SEQUENCE: 46
acctgtagcg ggccaacaac tctccaccag gggctt                                    36

<210> SEQ ID NO 47
<211> LENGTH: 19
<212> TYPE: DNA
<213> ORGANISM: Artificial
<220> FEATURE:
<223> OTHER INFORMATION: Nov-G2-F3* primer
<220> FEATURE:
<221> NAME/KEY: misc_feature
<222> LOCATION: (17)..(17)
<223> OTHER INFORMATION: N is an A or G

<400> SEQUENCE: 47
cccatctgat gggtccnca                                                       19

<210> SEQ ID NO 48
<211> LENGTH: 19
<212> TYPE: DNA
<213> ORGANISM: Artificial
<220> FEATURE:
<223> OTHER INFORMATION: Nov-G2-B3 primer

<400> SEQUENCE: 48
cacctggagc gtttctagg                                                       19
```